US 7,482,426 B2
Jan. 27, 2009

(12) United States Patent
Franz-Bacon et al.

(54) C23 POLYPEPTIDES

(75) Inventors: Karin Franz-Bacon, San Diego, CA (US); Daniel M. Gorman, Newark, CA (US); Terrill K. McClanahan, Sunnyvale, CA (US)

(73) Assignee: Schering Corporation, Kenilworth, NJ (US)

( * ) Notice: Subject to any disclaimer, the term of this patent is extended or adjusted under 35 U.S.C. 154(b) by 548 days.

(21) Appl. No.: 10/246,983

(22) Filed: Sep. 18, 2002

(65) Prior Publication Data

US 2003/0092123 A1    May 15, 2003

Related U.S. Application Data

(62) Division of application No. 09/099,898, filed on Jun. 18, 1998, now Pat. No. 6,503,730.

(60) Provisional application No. 60/050,156, filed on Jun. 19, 1997.

(51) Int. Cl.
- *C07K 5/00* (2006.01)
- *C07K 14/00* (2006.01)
- *C07K 14/52* (2006.01)
- *A61K 38/00* (2006.01)

(52) U.S. Cl. .................. 530/300; 530/324; 530/350; 530/351; 514/2

(58) Field of Classification Search .................. None
See application file for complete search history.

(56) References Cited

FOREIGN PATENT DOCUMENTS

| WO | WO 99/11293 | 3/1999 |
| WO | WO 01/40465 A2 | 6/2001 |

OTHER PUBLICATIONS

U.S. Appl. No. 10/246,853, filed Sep. 2002, Franz-Bacon et al.*
Li et al., Eur. J. Biochem., 1996, vol. 237(1):153-8.*
Ben-Baruch, A., Cancer Metastasis Rev., 2006, 25:357-371.*
Minami et al., Neuromolecular Med., 2005, 7(1-2):149-155 (abstract).*
Lees et al., Cancer Immunol. Immunother., 2000, 48(11):644-652 (abstract).*
M.D. Adams, et al., *GenBank*, Accession No. AA311223, Apr. 19, 1997. Definition: "EST181980 Jurkat T-cells V *Homo sapiens* cDNA 5' end. mRNA sequence."
Charles G. Garlisi, et al., *Clinical Immunology and Immunopathology*, 75(1):75-83, Apr. 1995. "T Cells Are Necessary for Th$_2$ Cytokine Production and Eosinophil Accumulation in Airways of Antigen-Challenged Allergic Mice".
L. Hillier, et al., *GenBank*, Accession No. N41594, Jan. 24, 1996. Definition: "yw66h04.r1 Soares_placenta_8to 9weeks_2NbHP8to9W *Homo sapiens* cDNA clone IMAGE:257239 5', mRNA sequence."
M. Marra, et al., *GenBank*, Accession No. AA097250, Oct. 25, 1996. Definition: "mk16a08.r1 Soares mouse p3NMF19.5 Mus musculus cDNA clone IMAGE:493046 5', mRNA sequence."
M. Marra, et al., *GenBank*, Accession No. AA139082, Feb. 16, 1997. Definition: "mr11g09.r1 Soares mouse 3NbMS Mus musculus cDNA clone IMAGE:597184 5', mRNA sequence."
M. Marra, et al., *GenBank*, Accession No. AA238901, Mar. 3, 1997. Definition: "my36g01.r1 Barstead mouse pooled organs MPLRB4 Mus musculus cDNA clone IMAGE:697968 5', mRNA sequence."
M. Marra, et al., *GenBank*, Accession No. AA238995, Mar. 3, 1997. Definition: "my39h08.r1 Barstead mouse pooled organs MPLRB4 Mus musculus cDNA clone IMAGE:698271 5', mRNA sequence."
M. Marra, et al., *GenBank*, Accession No. AA239013, Mar. 3, 1997. Definition: "my36h05.r1 Barstead mouse pooled organs MPLRB4 Mus musculus cDNA clone IMAGE:697977 5', mRNA sequence."
M. Marra, et al., *GenBank*, Accession No. AA239093, Mar. 3, 1997. Definition: "my34g06.r1 Barstead mouse pooled organs MPLRB4 Mus musculus cDNA clone IMAGE:697786 5', mRNA sequence."
M. Marra, et al., *GenBank*, Accession No. AA245405, Mar. 10, 1997. Definition: "my52f08.r1 Barstead mouse pooled organs MPLRB4 Mus musculus cDNA clone IMAGE:699495 5', mRNA sequence."
M. Marra, et al., *GenBank*, Accession No. AA245583, Mar. 10, 1997. Definition: "my52d07.r1 Barstead mouse pooled organs MPLRB4 Mus musculus cDNA clone IMAGE:699469 5', mRNA sequence."
M. Marra, et al., *GenBank*, Accession No. AA273994, Mar. 28, 1997. Definition: "vb70e06.r1 Barstead mouse pooled organs MPLRB4 Mus musculus cDNA clone IMAGE:762370 5', mRNA sequence."
M. Marra, et al., *GenBank*, Accession No. AA286376, Apr. 9, 1997. Definition: "vc48c04.r1 Soares mouse 3NbMS Mus musculus cDNA clone IMAGE:777798 5', mRNA sequence."
M. Marra, et al., *GenBank*, Accession No. AA423511, Oct. 16, 1997. Definition: "ve76b03.r1 Soares mouse mammary gland NbMMG Mus musculus cDNA clone IMAGE:832109 5', mRNA sequence."
M. Marra, et al., *GenBank*, Accession No. AA467519, Jun. 11, 1997. Definition: "ve01d11.r1 Soares mouse NbMH Mus musculus cDNA clone IMAGE:808821 5', mRNA sequence."
M. Marra, et al., *GenBank*, Accession No. AA471795, Jun. 18, 1997. Definition: "vg96c03.r1 Barstead mouse pooled organs MPLRB4 Mus musculus cDNA clone IMAGE:873796 5', mRNA sequence."
M. Marra, et al., *GenBank*, Accession No. AA472183, Jun. 18, 1997. Definition: "vg98d06.r1 Soares mouse mammary gland NbMMG Mus musculus cDNA clone IMAGE:873995 5', mRNA sequence."
M. Marra, et al., *GenBank*, Accession No. AA509615, Jul. 8, 1997. Definition: "vg19g08.r1 Soares mouse NbMH Mus musculus cDNA clone IMAGE:861854 5', mRNA sequence."
M. Marra, et al., *GenBank*, Accession No. AA512388, Jul. 8, 1997. Definition: "vj18d10.r1 Barstead mouse irradiated colon MPLRB7 Mus musculus cDNA clone IMAGE:922099 5', mRNA sequence."
M. Marra, et al., *GenBank*, Accession No. AA518124, Jul. 16, 1997. Definition: "vi23d10.r1 Barstead mouse irradiated colon MPLRB7 Mus musculus cDNA clone IMAGE:904627 5', mRNA sequence."

(Continued)

*Primary Examiner*—Elizabeth C. Kemmerer
*Assistant Examiner*—Xiaozhen Xie
(74) *Attorney, Agent, or Firm*—Edwin P. Ching; Gregory R. Bellomy

(57) ABSTRACT

Nucleic acids encoding a new family of small cysteine rich soluble proteins, from a mammal, reagents related thereto, including specific antibodies, and purified proteins are described. Methods of using said reagents and related diagnostic kits are also provided.

7 Claims, No Drawings

OTHER PUBLICATIONS

M. Marra, et al., *GenBank*, Accession No. AA518140, Jul. 16, 1997. Definition: "vi23f06.r1 Barstead mouse irradiated colon MPLRB7 Mus musculus cDNA clone IMAGE:904643 5', mRNA sequence."

M. Marra, et al., *GenBank*, Accession No. AA518288, Jul. 16, 1997. Definition: "vi27h06.r1 Barstead mouse irradiated colon MPLRB7 Mus musculus cDNA clone IMAGE:905051 5', mRNA sequence."

M. Marra, et al., *GenBank*, Accession No. AA518807, Jul. 16, 1997. Definition: "vi23h02.r1 Barstead mouse irradiated colon MPLRB7 Mus musculus cDNA clone IMAGE:904659 5', mRNA sequence."

M. Marra, et al., *GenBank*, Accession No. AA519036, Jul. 16, 1997. Definition: "vi26d04.r1 Barstead mouse irradiated colon MPLRB7 Mus musculus cDNA clone IMAGE:904903 5', mRNA sequence."

M. Marra, et al., *GenBank*, Accession No. AA522114, Jul. 17, 1997. Definition: "vi25e04.r1 Barstead mouse irradiated colon MPLRB7 Mus musculus cDNA clone IMAGE:904830 5', mRNA sequence."

M. Marra, et al., *GenBank*, Accession No. W34958, Sep. 12, 1996. Definition: "mc34f06.r1 Soares mouse p3NMF19.5 Mus musculus cDNA clone IMAGE:350435 5', mRNA sequence."

M. Marra, et al., *GenBank*, Accession No. W42057, Sep. 11, 1996. Definition: "mb16d01.r1 Soares mouse p3NMF19.5 Mus musculus cDNA clone IMAGE:329569 5', mRNA sequence."

M. Marra, et al., *GenBank*, Accession No. W42069, Sep. 11, 1996. Definition: "mb16d04.r1 Soares mouse p3NMF19.5 Mus musculus cDNA clone IMAGE:329575 5', mRNA sequence."

M. Marra, et al., *GenBank*, Accession No. W09755, Oct. 2, 1997. Definition: "ma56d06.r1 Soares mouse p3NMF19.5 Mus musculus cDNA clone IMAGE:314699 5', mRNA sequence."

NCI-CGAP, *GenBank*, Accession No. AA515389, Aug. 19, 1997. Definition: "nf65c03.s1 NCI_CGAP_Co3 *Homo sapiens* cDNA clone IMAGE:924772 3', mRNA sequence."

NCI-CGAP, *GenBank*, Accession No. AA524300, Aug. 21, 1997. Definition: "ng32g12.s1 NCI_CGAP_Co3 *Homo sapiens* cDNA clone IMAGE:936550 3', mRNA sequence."

NCI-CGAP, *GenBank*, Accession No. AA570296, Sep. 9, 1997. Definition: "nm07c02.s1 NCI_CGAP_Co10 *Homo sapiens* cDNA clone IMAGE:1059507 3', mRNA sequence."

Database DGENE, Last updated Aug. 17, 1999, Result from sequence search using SEQ ID NO:2, as the query and citing Accession Nos. 1999P-Y12933, 1999P-W87710, 1999P-W87707, 1999P-W87708, 1999P-W87709,; Derwent Information Ltd., London.

Peer Bork, *Trends in Genetics*, 12(10):425-427, Oct. 1996. "Go hunting in sequence databases but watch out for traps".

Peer Bork, *Genome Research*, 10:398-400, esp p. 400, 1998. "Powers and pitfalls in sequence analysis: The 70% hurdle".

Tobias Doerks et al., *Trends in Genetics*, 14(6): 248-250, Jun. 1998. "Protein annotation: detective work for function prediction".

Toru Miyazake, et al., *J. Exp. Med.*, 189(2):413-422, Jan. 18, 1999. "Increased susceptibilty of thymocytes to apoptosis in mice lacking AIM, a novel murine macrophage-derived soluble factor belonging to the scavenger receptor cysteine-rich domain superfamily".

Jeffrey Skolnick & Jacqueline S. Fetrow, *Trends in Biotech.*, 18(1):34-39, esp. p. 36, 2000. "From Genes to protein structure and function: novel applications of computational approaches in the genomic era".

Temple F. Smith & Xiaolin Zhang, *Bioinformatics*, 15:1222-1223, Nov. 1997. "The challenges of genome sequence annotation or "The devil is in the Details"".

Adams, et al. (1997) *Nature* 377(6547):3-174 "Initial assessment of human gene diversity and expression patterns based upon 83 million nucleotides of cDNA sequences".

Boussiotis, et al. (2001) *Blood* 97(2):565-571 "Altered T-cell receptor + CD28-mediated signaling and blocked cell cycle progression in interleukin 10 and transforming growth factor-β-treated alloreactive T cells that do not induce graft-versus-host disease".

Campo, et al. (2001) *Biological Trace Element Research* 79:15-22 "Zinc inhibits the mixed lymphocyte culture".

Kahan (1992) *Current Opinion in Immunology* 4:553-560 "Immunosuppressive therapy".

Piccotti, et al. (1999) *Transplantation* 67:1453-1460 "Interleukin-12 (IL-12)-driven alloimmune responses in vitro and in vivo".

Steppan and Lazar (2004) *Journal of Internal Medicine* 255:439-447 "The current biology of resistin".

Thomas, et al. (eds) (1999) *Hematopoietic Cell Transplantation*, Blackwell Science, Inc., Malden, MA, pp. 305-315.

Waalen, et al. (1987) *Scan. J. Immunol.* 26:525-533 "Characteristics of Human Rheumatoid Synovial and Normal Blood Dendritic Cells". Sequence Alignment of PRO1199 (SEQ ID NO: 6 of WO 01/40465) vs CRSP (SEQ ID NO: 2 of USSN 09/099,898).

* cited by examiner

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
        (A) LENGTH: 453 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 47..370

(ix) FEATURE:
        (A) NAME/KEY: mat_peptide
        (B) LOCATION: 101..370

(xi) SEQUENCE DESCRIPTION: SEQ ID NO: 1:

```
GTGTGCCGGA TTTGGTTAGC TGAGCCCACC GAGAGGCGCC TGCAGG ATG AAA GCT           55
                                                Met Lys Ala
                                                -18

CTC TGT CTC CTC CTC CTC CCT GTC CTG GGG CTG TTG GTG TCT AGC AAG        103
Leu Cys Leu Leu Leu Leu Pro Val Leu Gly Leu Leu Val Ser Ser Lys
-15             -10             -5                              1

ACC CTG TGC TCC ATG GAA GAA GCC ATC AAT GAG AGG ATC CAG GAG GTC        151
Thr Leu Cys Ser Met Glu Glu Ala Ile Asn Glu Arg Ile Gln Glu Val
            5                   10                  15

GCC GGC TCC CTA ATA TTT AGG GCA ATA AGC AGC ATT GGC CTG GAG TGC        199
Ala Gly Ser Leu Ile Phe Arg Ala Ile Ser Ser Ile Gly Leu Glu Cys
            20                  25                  30

CAG AGC GTC ACC TCC AGG GGG GAC CTG GCT ACT TGC CCC CGA GGC TTC        247
Gln Ser Val Thr Ser Arg Gly Asp Leu Ala Thr Cys Pro Arg Gly Phe
            35                  40                  45

GCC GTC ACC GGC TGC ACT TGT GGC TCC GCC TGT GGC TCG TGG GAT GTG        295
Ala Val Thr Gly Cys Thr Cys Gly Ser Ala Cys Gly Ser Trp Asp Val
50                  55                  60                  65

CGC GCC GAG ACC ACA TGT CAC TGC CAG TGC GCG GGC ATG GAC TGG ACC        343
Arg Ala Glu Thr Thr Cys His Cys Gln Cys Ala Gly Met Asp Trp Thr
                    70                  75                  80

GGA GCG CGC TGC TGT CGT GTG CAG CCC TGAGGTCGCG CGCAGCGCGT              390
Gly Ala Arg Cys Cys Arg Val Gln Pro
                85                  90

GCACAGCGCG GGCGGAGGCG GCTCCAGGTC CGGAGGGGTT GCGGGGAGC TGGAAATAAA       450

CCT                                                                    453
```

(2) INFORMATION FOR SEQ ID NO: 2:

```
        (i) SEQUENCE CHARACTERISTICS:
            (A) LENGTH: 108 amino acids
            (B) TYPE: amino acid
            (D) TOPOLOGY: linear (ii) MOLECULE TYPE: protein (xi) SEQUENCE DESCRIPTION: SEQ ID NO: 2:

Met Lys Ala Leu Cys Leu Leu Leu Leu Pro Val Leu Gly Leu Leu Val
-18         -15                 -10                 -5

Ser Ser Lys Thr Leu Cys Ser Met Glu Glu Ala Ile Asn Glu Arg Ile
         1           5                    10

Gln Glu Val Ala Gly Ser Leu Ile Phe Arg Ala Ile Ser Ser Ile Gly
 15              20                  25                      30

Leu Glu Cys Gln Ser Val Thr Ser Arg Gly Asp Leu Ala Thr Cys Pro
             35                  40                  45

Arg Gly Phe Ala Val Thr Gly Cys Thr Cys Gly Ser Ala Cys Gly Ser
             50                  55                  60

Trp Asp Val Arg Ala Glu Thr Thr Cys His Cys Gln Cys Ala Gly Met
             65                  70                  75

Asp Trp Thr Gly Ala Arg Cys Cys Arg Val Gln Pro
             80                  85              90

(2) INFORMATION FOR SEQ ID NO: 3:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 3:

TGTGGCTHYG SCTGTGGMTC KTGG                                              24

(2) INFORMATION FOR SEQ ID NO: 4:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 4:

CAGCAGCGSG CWSHKGTCCA GTC                                               23
```

C23 POLYPEPTIDES

This filing claims benefit of U.S. patent application Ser. No. 09/099,898, filed Jun. 18, 1998, now U.S. Pat. No. 6,503, 730, and U.S. Provisional Patent Application No. 60/050,156, filed Jun. 19, 1997, which are incorporated herein by reference.

FIELD OF THE INVENTION

The present invention contemplates compositions related to proteins which function in modulating animal physiology, e.g., controlling development, differentiation, trafficking, and physiology of mammalian cells, e.g., cells of a mammalian immune system. In particular, it provides purified genes, proteins, antibodies, and related reagents useful, e.g., to regulate activation, development, differentiation, and function of various cell types, particularly primate cells.

BACKGROUND OF THE INVENTION

The circulating component of the mammalian circulatory system comprises various cell types, including red and white blood cells of the erythroid and myeloid cell lineages. See, e.g., Rapaport (1987) *Introduction to Hematology* (2d ed.) Lippincott, Philadelphia, Pa.; Jandl (1987) *Blood: Textbook of Hematology,* Little, Brown and Co., Boston, Mass.; and Paul (ed.) (1993) *Fundamental Immunology* (3d ed.) Raven Press, NY.

Growth factors, which are typically proteins, influence cellular proliferation and/or differentiation. Usually their effects are mediated through a cell membrane receptor. Some growth factors function via an autocrine signal. The growth factors have varying ranges of specificity of target cells. For example, certain factors play roles in oogenesis, see, e.g., Padgett, et al. (1987) *Nature* 325:81-84; Ferguson, et al. (1992) *Cell* 71:451-461; Staehling-Hampton, et al. (1994) *Nature* 372: 783-786; and Panganiban, et al. (1990) *Mol. Cell. Biol.* 10:2669-2677, in embryogenesis, see, e.g., Xie, et al. (1994) *Science* 263:1756-1759; Raz, et al. (1993) *Genes and Development* 7:1937-1948; Brand, et al. (1994) *Genes and Development* 8:629-639; Goode, et al. (1992) *Development* 116: 177-192; Livneh, et al. (1985) *Cell* 40:599-607; and Neuman-Silberberg, et al. (1993) *Cell* 75:164-174; and in morphogenesis, see, e.g., Heberlein, et al. (1993) *Cell* 75:913-926; Nellen, et al. (1994) *Cell* 78:225-237; Brummel, et al. (1994) *Cell* 78:251-261; and Penton, et al. (1994) *Cell* 78:239-250; of specific cell types or organs.

For some time, it has been known that the mammalian immune response is based on a series of complex cellular interactions, called the "immune network." Recent research has provided new insights into the inner workings of this network. While it remains clear that much of the response does, in fact, revolve around the network-like interactions of lymphocytes, macrophages, granulocytes, and other cells, immunologists now generally hold the opinion that soluble proteins, known as lymphokines, cytokines, or monokines, play a critical role in controlling these cellular interactions. Thus, there is considerable interest in the isolation, characterization, and mechanisms of action of cell modulatory factors, an understanding of which should lead to significant advancements in the diagnosis and therapy of numerous medical abnormalities, e.g., immune system and other disorders.

Lymphokines apparently mediate cellular activities in a variety of ways. They have been shown to support the proliferation, growth, and differentiation of the pluripotential hematopoietic stem cells into vast numbers of progenitors comprising diverse cellular lineages making up a complex immune system. These interactions between the cellular components are necessary for a healthy immune response. These different cellular lineages often respond in a different manner when lymphokines are administered in conjunction with other agents.

The chemokines are a large and diverse superfamily of proteins. The superfamily is subdivided into three branches, based upon whether the first two cysteines in the classical chemokine motif are adjacent (termed the "C—C" branch) or spaced by an intervening residue ("C—X—C"), or a new branch which lacks two cysteines in the corresponding motif, represented by the chemokines known as lymphotactins. See, e.g., Schall and Bacon (1994) *Current Opinion in Immunology* 6:865-873; and Bacon and Schall (1996) *Int. Arch. Allergy & Immunol.* 109:97-109.

There is considerable interest in the isolation, characterization, and mechanisms of action of modulatory factors. Many factors have been identified which influence the differentiation process of precursor cells, or regulate the physiology or migration properties of specific cell types. These observations indicate that other factors exist whose functions in immune function were heretofore unrecognized. These factors provide for biological activities whose spectra of effects may be distinct from known differentiation or activation factors. The absence of knowledge about the structural, biological, and physiological properties of the regulatory factors which regulate cell physiology in vivo prevents the modification of the effects of such factors. Thus, medical conditions where regulation of the development or physiology of relevant cells is required remains unmanageable.

SUMMARY OF THE INVENTION

The present invention reveals the existence of a new family of Cysteine Rich Soluble Proteins (CRSPs). Their expression suggests a role in immunological function, particularly in inflammatory conditions. It is characterized in various rodent and human embodiments. See also U.S. Ser. No. 09/099,836, filed Jun. 18, 1998; Ser. No. 08/878,730, filed Jun. 19, 1997; and U.S. Ser. No. 60/061,641, filed Oct. 9, 1997; each of which is incorporated herein by reference. Structural similarity to the defensins, along with expression levels, suggest a direct antimicrobial function, e.g., microbiostatic or microbiocidal.

The present invention comprises a composition of matter selected from: a substantially pure or recombinant C23 protein or peptide exhibiting identity over a length of at least 12 amino acids to SEQ ID NO: 2; a natural sequence C23 of SEQ ID NO: 2; or a fusion protein comprising C23 sequence. In certain embodiments, the protein comprises a segment exhibiting sequence identity to a corresponding portion of a C23, wherein: the identity is over at least about 15 amino acids; the identity is over at least 19 amino acids; or the identity is over at least 25 amino acids. In other embodiments, the: C23 comprises a mature sequence of Table 1; or protein or peptide: is from a warm blooded animal selected from a mammal, including a primate; comprises at least one polypeptide segment of SEQ ID NO: 2; exhibits a plurality of portions exhibiting said identity; is a natural allelic variant of C23; has a length at least about 30 amino acids; exhibits at least two non-overlapping epitopes which are specific for a mammalian C23; exhibits a sequence identity at least about 90% over a length of at least about 20 amino acids to a primate C23; exhibits at least two non-overlapping epitopes which are specific for a primate C23; exhibits a sequence identity over a length of at least about 20 amino acids to a primate C23; is glycosylated; has a molecular weight of at least 7 kD with natural glycosylation; is a synthetic polypeptide; is attached to a solid substrate; is conjugated to another chemical moiety; is a 5-fold or less substitution from natural sequence; or is a deletion or insertion variant from a natural sequence. Preferably, the composition can comprise: a sterile C23 protein or peptide; or the C2 protein or peptide and a carrier, wherein said carrier is: an aqueous compound, including water, saline, and/or buffer; and/or formulated for oral, rectal, nasal, topical, or parenteral administration.

Various fusion protein embodiments may comprise: mature protein sequence of Table 1; a detection or purification tag, including a FLAG® expression system tag sequence, His6, or Ig sequence; or sequence of another cytokine or growth factor protein.

Certain kits will comprise a C23 protein or polypeptide, and: a compartment comprising said protein or polypeptide; and/or instructions for use or disposal of reagents in the kit.

Binding compounds are also provided, including a binding compound comprising an antigen binding portion from an antibody, which specifically binds to a natural C23 protein, wherein: the protein is a primate protein; the binding compound is an Fv, Fab, or Fab2 fragment; the binding compound is conjugated to another chemical moiety; or the antibody: is raised against a peptide sequence of a mature polypeptide of Table 1; is raised against a mature C23; is raised to a purified C23; is immunoselected; is a polyclonal antibody; binds to a denatured C23; exhibits a Kd to antigen of at least 30 µM; is attached to a solid substrate, including a bead or plastic membrane; is in a sterile composition; or is detectably labeled, including a radioactive or fluorescent label. The invention further provides a kit comprising the binding compound, and: a compartment comprising said binding compound; and/or instructions for use or disposal of reagents in said kit. Preferably, the kit is capable of making a qualitative or quantitative analysis. Other embodiments include a composition comprising: a sterile binding compound of Claim 7, or b) said binding compound and a carrier, wherein said carrier is: an aqueous compound, including water, saline, and/or buffer; and/or formulated for oral, rectal, nasal, topical, or parenteral administration.

Nucleic acid embodiments include an isolated or recombinant nucleic acid encoding a protein or peptide or fusion protein, wherein: the C family protein is from a mammal, including a primate; or the nucleic acid: encodes an antigenic peptide sequence of Table 1; encodes a plurality of antigenic peptide sequences of Table 1; exhibits at least about 80% identity to a natural cDNA encoding the segment; is an expression vector; further comprises an origin of replication; is from a natural source; comprises a detectable label; comprises synthetic nucleotide sequence; is less than 6 kb, preferably less than 3 kb; is from a mammal, including a primate; comprises a natural full length coding sequence; is a hybridization probe for a gene encoding said C family protein; or is a PCR primer, PCR product, or mutagenesis primer.

Certain cell embodiments which comprise a recombinant nucleic acid are provided, and preferably the cell is: a prokaryotic cell; a eukaryotic cell; a bacterial cell; a yeast cell; an insect cell; a mammalian cell; a mouse cell; a primate cell; or a human cell. Kits are provided, including those comprising such a nucleic acid, and: a compartment comprising the nucleic acid; a compartment further comprising a C23 protein or polypeptide; and/or instructions for use or disposal of reagents in the kit. Preferably, the kit is capable of making a qualitative or quantitative analysis.

Other nucleic acid embodiments include ones which: hybridize under wash conditions of 30° C. and less than 2M salt to SEQ ID NO: 1; where the wash conditions are-at 45° C. and/or 500 mM salt; where the wash conditions are at 55° C. and/or 150 mM salt; or exhibit at least about 85% identity over a stretch of at least about 30 nucleotides to a primate C23; or the identity is at least 90% and/or the stretch is at least 55 nucleotides; or where the identity is at least 95% and/or the stretch is at least 75 nucleotides.

The invention also provides a method of modulating physiology or development of a cell or tissue culture cells comprising contacting said cell with an agonist or antagonist of a C23.

DETAILED DESCRIPTION

All references cited herein are incorporated herein by reference to the same extent as if each individual publication or patent application was specifically and individually indicated to be incorporated by reference.

| OUTLINE | |
|---|---|
| I. | General |
| II. | Definitions |
| III. | Nucleic Acids |
| IV. | Making CRSP Family Proteins |
| V. | Antibodies |
| | a. antibody production |
| | b. immunoassays |
| VI. | Purified CRS Proteins |
| VII. | Physical Variants |
| VIII. | Binding Agent:CRSP Complexes |
| IX. | Functional Variants |
| X. | Uses |
| XI. | Kits |
| XII. | Receptor Isolation |

I. General

The present invention provides DNA sequences encoding soluble mammalian proteins which exhibit structural properties or motifs characteristic of a small soluble protein, e.g., a defensin, growth factor, cytokine, or chemokine. Because the proteins are cyteine rich, and the cysteine motifs appear conserved, these proteins are referred to as Cysteine Rich Soluble Proteins (CRSPs). The tissue expression distribution of these proteins correlate with significant medical conditions.

For reviews on the defensins, see, e.g., Ganz, et al. (1998) *Current Op. in Immunol.* 10:41-44; Hancock, et al. (1998) *Trends Biotech.* 16:82-88; Lehrer, et al. (1996) *Ann. NY Acad. Sci.* 797:228-239; White, et al. (1995) *Current Op. Struct. Biol.* 5:521-527; Ganz, et al. (1995) *Pharmacol. Ther.* 66:191-205; Harwig, et al. (1994) *Methods in Enzymology* 236:160-172; and Lehrer, et al. (1993) *Ann. Rev. Immunol.* 11:105-128. The defensins exhibit significant sequence similarity to the carboxy terminus of the CRSPs. Processing of the defensins from inactive precursors follows a known pathway. The amounts of protein expressed and the exon structure of the defensins seems to match with that of the CRSPs.

For a review of the cytokines, see, e.g., Thompson (1994) *The Cytokine Handbook* 2d ed., Academic Press, San Diego; and Aggarwal and Gutterman (1992) *Human Cytokines: Handbook for Basic and Clinical Research,* Blackwell Pub., Oxford. Many specific sequences and references are available, e.g., from the GenBank, and references providing gene and/or cytokine amino acid sequence. Many receptor sequences are also available from GenBank. See also Howard, et al. (1993) in Paul (ed.) (1993) *Fundamental Immunology* (3d ed.) Raven Press, NY.

For reviews of the chemokine family, see, e.g., Lodi, et al. (1994) *Science* 263:1762-1767; Gronenborn and Clore (1991) *Protein Engineering* 4:263-269; Miller and Kranger (1992) *Proc. Nat'l Acad. Sci. USA* 89:2950-2954; Matsushima and Oppenheim (1989) *Cytokine* 1:2-13; Stoeckle and Baker (1990) *New Biol.* 2:313-323; Oppenheim, et al. (1991) *Ann. Rev. Immunol.* 9:617-648; Schall (1991) *Cytokine* 3:165-183; and *The Cytokine Handbook* Academic Press, NY. The proteins described herein are designated Cysteine Rich Soluble Proteins because they were initially recognized as soluble proteins. These proteins share a highly conserved pattern of cysteine motifs, e.g., structural motifs, distinct from the other known groups of soluble protein molecules.

The best characterized embodiment of this family of proteins were discovered from a human sequence source. See Table 1. The descriptions below are directed, for exemplary purposes, to primate embodiments, e.g., human, but are likewise applicable to related embodiments from other, e.g., natural, sources. These sources should include various vertebrates, typically warm blooded animals, e.g., birds and mammals, particularly domestic animals, and primates.

The CRSPs of this invention are defined in part by their physicochemical and structural properties. The biological properties of the primate, e.g., human CRSP described herein, are defined by their amino acid sequence, and mature size. One of skill will readily recognize that some sequence variations may be tolerated, e.g., conservative substitutions or positions remote from the helical structures, without altering significantly the biological activity of the molecule. The cysteines, being conserved across family members, are probably relatively important structurally. It is likely that most, or all, of them are disulfide linked in important pairings.

The cysteine rich nature makes the protein a good substrate for sulfhydryl reagents. It will be useful as a control for cysteine incorporation, and as a sample to test ability to sequence through those residues. The protein will also find use as a carbon source.

In addition, the label may refer, in specific embodiments, to the nucleic acids which may be isolated using PCR amplification from appropriate cells of sequences using primers which flank the sequences described. Thus, even if minor errors in the given sequences may have resulted from ambi-

TABLE 1

Human nucleic acid sequence (SEQ ID NO:1) and corresponding amino acid sequence (SEQ ID NO:2) of cysteine rich soluble protein 23 (C23). Coding sequence begins at about nucleotide 47 and ends at about nucleotide 370 (end of last coding codon before the termination). Putative signal peptide runs from amino acid -18 (Met) to about predicted -1 (Ser). Mature sequence has signal sequence removed. Helical structures run from mature protein residues 5 (Ser) to 18 (Ala). β sheet structures run from about 31 (Leu) to 37 (Thr); 42 (Leu) to 44 (Thr); 50 (Ala) to 53 (Gly); 63 (Trp) to 66 (Arg); 71 (Cys) to 75 (Cys); and 86 (Cys) to 89 (Gln). Structure is based upon use of PHD program: accessed by http://www.embl-heidelberg.de/predictprotein/; or by the DSC program: accessed by http://bonsai.lif.icnet.uk/bmm/dsc/. Introns likely about 164-165, and 242-243.

```
GTGTGCCGGA TTTGGTTAGC TGAGCCCACC GAGAGGCGCC TGCAGG ATG AAA GCT      55
                                                    Met Lys Ala
                                                     -18

CTC TGT CTC CTC CTC CTC CCT GTC CTG GGG CTG TTG GTG TCT AGC AAG    103
Leu Cys Leu Leu Leu Leu Pro Val Leu Gly Leu Leu Val Ser Ser Lys
-15              -10                  -5                        1

ACC CTG TGC TCC ATG GAA GAA GCC ATC AAT GAG AGG ATC CAG GAG GTC    151
Thr Leu Cys Ser Met Glu Glu Ala Ile Asn Glu Arg Ile Gln Glu Val
             5                   10                  15

GCC GGC TCC CTA ATA TTT AGG GCA ATA AGC AGC ATT GGC CTG GAG TGC    199
Ala Gly Ser Leu Ile Phe Arg Ala Ile Ser Ser Ile Gly Leu Glu Cys
            20                  25                  30

CAG AGC GTC ACC TCC AGG GGG GAC CTG GCT ACT TGC CCC CGA GGC TTC    247
Gln Ser Val Thr Ser Arg Gly Asp Leu Ala Thr Cys Pro Arg Gly Phe
         35                  40                  45

GCC GTC ACC GGC TGC ACT TGT GGC TCC GCC TGT GGC TCG TGG GAT GTG    295
Ala Val Thr Gly Cys Thr Cys Gly Ser Ala Cys Gly Ser Trp Asp Val
50                  55                  60                  65

CGC GCC GAG ACC ACA TGT CAC TGC CAG TGC GCG GGC ATG GAC TGG ACC    343
Arg Ala Glu Thr Thr Cys His Cys Gln Cys Ala Gly Met Asp Trp Thr
                 70                  75                  80

GGA GCG CGC TGC TGT CGT GTG CAG CCC TGAGGTCGCG CGCAGCGCGT          390
Gly Ala Arg Cys Cys Arg Val Gln Pro
                 85                  90

GCACAGCGCG GCGGAGGCG GCTCCAGGTC CGGAGGGGTT GCGGGGAGC TGGAAATAAA    450

CCT                                                                453
``` guities or uncertainties in sequencing, the PCR technology will allow isolation of natural isolates of the described genes. In addition, the nucleotide sequences in the regions corresponding to C23 residues 56-63 and 79-86 are highly conserved across the known class members. It is likely that additional human embodiments will be found using appropriate PCR primers encoding such regions.

CRSPs are present in specific tissue types, as described below. Each correlates with important conditions, which are suggestive of important roles in immunological conditions. The interaction of the protein with a receptor is likely to be important for mediating various aspects of cellular physiology or development. The cellular types which express message encoding CRSPs suggest that signals important in cell differentiation and development are mediated by them. See, e.g., Gilbert (1991) *Developmental Biology* (3d ed.) Sinauer Associates, Sunderland, Mass.; Browder, et al. (1991) *Developmental Biology* (3d ed.) Saunders, Philadelphia, Pa.; Russo, et al. (1992) *Development: The Molecular Genetic Approach* Springer-Verlag, New York, N.Y.; and Wilkins (1993) *Genetic Analysis of Animal Development* (2d ed.) Wiley-Liss, New York, N.Y. Moreover, CRSP expression correlates with certain specific conditions. See below.

The CRSP producing profile of different cell types is elucidated herein. These observations suggest that the CRSPs represent novel additions to the chemokine/growth factor superfamily.

CRSP protein biochemistry was assessed in some mammalian expression systems. CRSP member C23 was produced as a protein of Mr ~8 kDa as evaluated by reducing SDS-PAGE; control transfected supernatants contained no such species. The absence of glycosylation motifs suggests that the natural protein is not glycosylated, and that recombinant protein forms lacking natural glycosylation should share similar biological activity.

Since the structure of the proteins are soluble, it is likely that the entire spectrum of inflammatory, infectious, and immunoregulatory states thought to involve other related cytokines or growth factors may function through such proteins.

II. Definitions

The term "binding composition" refers to molecules that bind with specificity to a CRSP, e.g., in an antibody-antigen interaction. However, other compounds, e.g., receptor proteins, may also specifically associate with CRSPs at a higher affinity and/or specificity than other molecules. Typically, the association will be in a natural physiologically relevant protein-protein interaction, either covalent or non-covalent, and may include members of a multiprotein complex, including carrier compounds or dimerization partners. The molecule may be a polymer, e.g., protein, or chemical reagent. No implication as to whether a CRSP is either a concave or convex surface in a ligand or a receptor of a ligand-receptor interaction is necessarily represented, other than whether the interaction exhibits similar specificity, e.g., specific affinity. A functional analog may be a ligand with structural modifications, e.g., sequence substitutions, often conservative residues, or modified, e.g., derivatized protein polymer, or may be a wholly unrelated molecule, e.g., which has a molecular shape which interacts with the appropriate ligand binding determinants. The ligands may serve as agonists or antagonists of the receptor, see, e.g., Goodman, et al. (eds.) (1990) *Goodman & Gilman's: The Pharmacological Bases of Therapeutics* (8th ed.) Pergamon Press, Tarrytown, N.Y.

The term "binding agent:CRSP complex", as used herein, refers to a complex of a binding agent and a CRSP that is formed by specific binding of the binding agent to the CRSP. Specific binding of the binding agent means that the binding agent has a specific binding site that recognizes a site on the CRSP protein. For example, antibodies raised to a CRSP protein and recognizing an epitope on the CRSP protein are capable of forming a binding agent:CRSP complex by specific binding. Typically, the formation of a binding agent: CRSP complex allows the measurement of CRSP in a mixture of other proteins and biologics. The term "antibody:CRSP complex" refers to an embodiment in which the binding agent is an antibody. The antibody may be monoclonal, polyclonal, or a binding fragment of an antibody, e.g, an Fv, Fab, or F(ab)2 fragment, or even a single chain antibody form. The antibody will often preferably be a polyclonal antibody for cross-reactivity purposes.

"Homologous" nucleic acid sequences, when compared, exhibit significant similarity. The standards for homology in nucleic acids are either measures for homology generally used in the art by sequence comparison and/or phylogenetic relationship, or based upon hybridization conditions. Hybridization conditions are described in greater detail below.

An "isolated" nucleic acid is a nucleic acid, e.g., an RNA, DNA, or a mixed polymer, which is substantially separated from other biologic components which naturally accompany a native sequence, e.g., proteins and flanking genomic sequences from the originating species. The term embraces a nucleic acid sequence which has been removed from its naturally occurring environment, and includes recombinant or cloned DNA isolates and chemically synthesized analogs, or analogs biologically synthesized by heterologous systems. A substantially pure molecule includes isolated forms of the molecule. An isolated nucleic acid will usually contain homogeneous nucleic acid molecules, but will, in some embodiments, contain nucleic acids with minor sequence heterogeneity. This heterogeneity is typically found at the polymer ends or portions not critical to a desired biological function or activity.

As used herein, the term "CRSP" shall encompass various specific embodiments, e.g., when used in a protein context, a protein having amino acid sequences, particularly from the cysteine containing portions, shown in SEQ ID NO: 2, or a significant fragment of such a protein. The invention also embraces a polypeptide which exhibits similar structure to primate, e.g., human CRSP, e.g., which interacts with CRSP specific binding components. These binding components, e.g., antibodies, typically bind to a CRSP with high affinity, e.g., at least about 100 nM, usually better than about 30 nM, preferably better than about 10 nM, and more preferably at better than about 3 nM.

The term "polypeptide" or "protein" as used herein includes a significant fragment or segment of the conserved cysteine containing portions of a CRSP, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids, e.g., 35, 40, 45, 50, 60, 70, 80, etc. Particularly important segments include those which span over regions between, e.g., the residues corresponding to C23 residues 33-86, or significant portions thereof. Thus, fragments corresponding to ends beginning at 34, 35, 36, 37, etc., and ending, e.g., at positions 85, 84, 83, 82, 81, 80, 79, 78, 77, etc., will be interesting. Antigenic fragments will be utilized, e.g., in generating antibody reagents.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection and/or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any non-naturally occurring vector is encompassed, as are nucleic acids comprising sequence derived using any synthetic oligonucleotide process. Such is often done to replace a codon with a redundant codon encoding the same or a similar amino acid, while typically introducing or removing a sequence recognition site. Preferred embodiments include, e.g., 1-fold, 2-fold, 3-fold, 5-fold, 7-fold, etc, preferably conservative substitutions at the nucleotide or amino acid levels. Preferably the substitutions will be away from the conserved cysteines, and often will be in the regions away from the helical structural domains. Such variants may be useful to produce specific antibodies, and often will share many or all biological properties.

Alternatively, recombinant manipulation is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

"Solubility" is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.) W.H. Freeman & Co., San Francisco, Calif.; and Cantor and Schimmel (1980) *Biophysical Chemistry* parts 1-3, W.H. Freeman & Co., San Francisco, Calif. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30S, more typically less than about 15S, usually less than about 10S, more usually less than about 6S, and, in particular embodiments, preferably less than about 4S, and more preferably less than about 3S. Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions. In other contexts, the protein may be denatured, e.g., in Western protein blot analysis, or to minimize certain tertiary conformation features of sequences.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS (cholesteryl hemisuccinate) or CHAPS (3-[3-cholamidopropyl)dimethylammonio]-1-propane sulfonate), or a low enough concentration as to avoid significant disruption of structural or physiological properties of the protein. Sterile compositions are often useful, e.g., in a tissue culture assay context.

"Substantially pure" in a protein context typically means that the protein is isolated from other contaminating proteins, nucleic acids, and other biologicals derived from the original, e.g., natural, source organism. Purity, or "isolation" may be assayed by standard methods, and will ordinarily be at least about 50% pure, more ordinarily at least about 60% pure, generally at least about 70% pure, more generally at least about 80% pure, often at least about 85% pure, more often at least about 90% pure, preferably at least about 95% pure, more preferably at least about 98% pure, and in most preferred embodiments, at least 99% pure. The measure will typically be by mass, but may be molar. Similar concepts apply, e.g., to antibodies or nucleic acids.

"Substantial similarity" in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial similarity exists when the segments will hybridize under selective hybridization conditions, to a strand, or its complement, typically using a sequence derived from SEQ ID NO: 1. Typically, selective hybridization will occur when there is at least about 55% similarity over a stretch of at least about 30 nucleotides, preferably at least about 65% over a stretch of at least about 25 nucleotides, more preferably at least about 75%, and most preferably at least about 90% over about 20 nucleotides. See Kanehisa (1984) *Nuc. Acids Res.* 12:203-213. The length of similarity comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides, e.g., 150, 200, etc.

"Stringent conditions", in referring to homology or substantial similarity in the hybridization context, will be stringent combined conditions of salt, temperature, organic solvents, and other parameters, typically those controlled in hybridization reactions. The combination of parameters is more important than the measure of any single parameter. See, e.g., Wetmur and Davidson (1968) *J. Mol. Biol.* 31:349-370. A nucleic acid probe which binds to a target nucleic acid under stringent conditions is specific, e.g., for hybridizing to said target nucleic acid. Such a probe is typically more than 11 nucleotides in length, and is sufficiently identical or complementary to a target nucleic acid over the region specified by the sequence of the probe to bind the target under stringent hybridization conditions. PCR primers are often prime examples of embodiments where specificity of relatively short sequence segments will be used.

CRSPs from other mammalian species can be cloned and isolated by cross-species hybridization of closely related species. See, e.g., below. Alternatively, other related proteins may be isolated by protein purification or antigenic methods using cross-reacting antibody reagents. It also appears that the genes may be genomically clustered within a species, so other members of the family may be isolated by positional cloning techniques upon identification of one embodiment. Similarity may be relatively low between distantly related species, and thus hybridization of relatively closely related species is advisable. Alternatively, preparation of an antibody preparation which exhibits less species specificity may be useful in expression cloning or protein isolation approaches.

The phrase "specifically binds to an antibody" or "specifically immunoreactive with", when referring to a protein or peptide, refers to a binding reaction which is determinative of the presence of the protein in the presence of a heterogeneous population of proteins and other biological components. Thus, under designated immunoassay conditions, the specified antibodies bind to a particular protein and do not significantly bind other proteins present in the sample. Specific binding to an antibody under such conditions may require an antibody that is selected for its specificity for a particular protein. For example, antibodies raised to a primate CRSP immunogen with the amino acid sequence depicted in SEQ ID NO: 2 can be selected to obtain antibodies specifically immunoreactive with CRSP proteins and not with other proteins. These antibodies will recognize proteins highly similar to a homologous CRSP protein or proteins, as selected.

III. Nucleic Acids

This C23 human CRSP is exemplary of a larger class of structurally and functionally related proteins. These soluble proteins will likely serve to transmit signals between different cell types. The preferred embodiments, as disclosed, will be useful in standard procedures to isolate genes from different individuals or other species, e.g., warm blooded animals, such as birds and mammals. Cross hybridization or other techniques will allow isolation of related genes encoding proteins from individuals, strains, or species. In fact, Applicants possess specific data that this gene hybridizes across species to mouse embodiments. A number of different approaches are available to successfully isolate a suitable nucleic acid clone based upon the information provided herein.

While the overall coding sequence identity among mouse family members is in the 40% range overall, specific portions exhibit over 80%. Southern blot hybridization studies using specific portions might qualitatively determine the presence of homologous genes in human, monkey, rat, dog, cow, and rabbit genomes under specific hybridization conditions. PCR techniques may be useful using, e.g., the conserved sequence regions, preferably at the nucleotide level, but perhaps also at the protein level.

Complementary sequences will also be used as probes or primers. Based upon identification of the likely amino terminus, other peptides should be particularly useful, e.g., coupled with anchored vector or poly-A complementary PCR techniques or with complementary DNA of other peptides.

Techniques for nucleic acid manipulation of genes encoding CRSP proteins, such as subcloning nucleic acid sequences encoding polypeptides into expression vectors, labeling probes, DNA hybridization, and the like are described generally in Sambrook, et al. (1989) *Molecular Cloning: A Laboratory Manual* (2nd ed.) Vol. 1-3, Cold Spring Harbor Laboratory, Cold Spring Harbor Press, NY, which is incorporated herein by reference. This manual is hereinafter referred to as "Sambrook, et al."

There are various methods of isolating DNA sequences encoding CRSPs. For example, DNA is isolated from a genomic or cDNA library using labeled oligonucleotide probes having sequences identical or complementary to the sequences disclosed herein. Full-length probes may be used, or oligonucleotide probes may be generated by comparison of the sequences disclosed. Such probes can be used directly in hybridization assays to isolate DNA encoding CRSPs, or probes can be designed for use in amplification techniques such as PCR, for the isolation of DNA encoding CRSPs. Certain genomic searches of available sequence databases, public or private, will also be useful to identify additional members.

To prepare a cDNA library, mRNA is isolated from cells which express a CRSP protein. cDNA is prepared from the mRNA and ligated into a recombinant vector. The vector is transfected into a recombinant host for propagation, screening, and cloning. Methods for making and screening cDNA libraries are well known. See Gubler and Hoffman (1983) *Gene* 25:263-269 and Sambrook, et al.

For a genomic library, e.g., the DNA can be extracted from tissue and either mechanically sheared or enzymatically digested to yield fragments of about 12-20 kb. The fragments are then separated by gradient centrifugation and cloned in bacteriophage lambda vectors. These vectors and phage are packaged in vitro, as described in Sambrook, et al. Recombinant phage are analyzed by plaque hybridization as described in Benton and Davis (1977) *Science* 196:180-182. Colony hybridization is carried out as generally described in e.g., Grunstein, et al. (1975) *Proc. Natl. Acad. Sci. USA.* 72:3961-3965. Modifications may be incorporated.

DNA encoding a CRSP can be identified in either cDNA or genomic libraries by its ability to hybridize with the nucleic acid probes described herein, e.g., in colony or plaque hybridization assays. The corresponding DNA regions are isolated by standard methods familiar to those of skill in the art. See, e.g., Sambrook, et al.

Various methods of amplifying target sequences, such as the polymerase chain reaction, can also be used to prepare DNA encoding CRSPs. Polymerase chain reaction (PCR) technology is used to amplify such nucleic acid sequences directly from mRNA, from cDNA, and from genomic libraries or cDNA libraries. The isolated sequences encoding CRSP proteins may also be used as templates for PCR amplification. The sequences provided teach many appropriate primers, and pairs.

Typically, in PCR techniques, oligonucleotide primers complementary to two 5' regions in the DNA region to be amplified are synthesized. The polymerase chain reaction is then carried out using the two primers. See Innis, et al. (eds.)

(1990) *PCR Protocols: A Guide to Methods and Applications* Academic Press, San Diego, Calif. Primers can be selected to amplify the entire regions encoding a full-length CRSP protein or to amplify smaller DNA segments as desired. Once such regions are PCR-amplified, they can be sequenced and oligonucleotide probes can be prepared from sequence obtained using standard techniques. These probes can then be used to isolate DNA's encoding CRSP proteins.

Oligonucleotides for use as probes are usually chemically synthesized according to the solid phase phosphoramidite triester method first described by Beaucage and Carruthers (1983) *Tetrahedron Lett.* 22(20):1859-1862, or using an automated synthesizer, as described in Needham-VanDevanter, et al. (1984) *Nucleic Acids Res.* 12:6159-6168. Purification of oligonucleotides is performed e.g., by native acrylamide gel electrophoresis or by anion-exchange HPLC as described in Pearson and Regnier (1983) *J. Chrom.* 255:137-149. The sequence of the synthetic oligonucleotide can be verified using, e.g., the chemical degradation method of Maxam, A. M. and Gilbert, W. in Grossman, L. and Moldave (eds.) (1980) *Methods in Enzymology* 65:499-560 Academic Press, New York.

An isolated nucleic acid encoding a human CRSP has been identified. The nucleotide sequence and corresponding open reading frame of this embodiment is provided in SEQ ID NO: 1.

Notably, the different genes of the family exhibit great conservation of spacing of the cysteine residues. In particular, the spacing is CX11CX8CXCX3CX10CXCXCX9CC. See Table 1.

Based upon the structural modeling and insights in the binding regions of the collective group, it is predicted that residues in the mature protein, lacking a signal of about 18 residues, exhibit structural features as described in Table 1. The soluble protein possesses one helical structure, and six beta strands. The structure suggests that the sheets form a plane, and that the underside of the plane is probably the receptor binding surface. Thus, residue substitutions at positions on the upper surface, or in the helical region away from the sheet surface will not affect biological activity.

Fragments of at least about 8-10 residues in the cysteine rich region would be especially interesting peptides, e.g., starting at residue positions of the mature protein 1, 2, 3, etc. However, the cysteine rich region begins at 33-86. Those fragments would typically end at the ends of the helical or sheet strands should be important. Other interesting peptides of various lengths would include ones which begin or end in other positions of the protein, e.g., at residues 87, 86, etc., with lengths ranging, e.g., from about 8 to 20, 25, 30, 35, 40, etc.

This invention provides isolated DNA or fragments to encode a CRSP protein. In addition, this invention provides isolated or recombinant DNA which encodes a protein or polypeptide which is capable of hybridizing under appropriate conditions, e.g., high stringency, with the DNA sequences described herein. Said biologically active protein or polypeptide can be an intact ligand, or fragment, and have an amino acid sequence as disclosed in SEQ ID NO: 2. Preferred embodiments will be full length natural sequences, from isolates, e.g., about 7-8K daltons in size when unglycosylated, or fragments of at least about 1,000 daltons, more preferably at least about 3,000 daltons. In glycosylated forms, which appear unnatural, the protein may be larger. Further, this invention contemplates the use of isolated or recombinant DNA, or fragments thereof, which encode proteins which are homologous to a CRSP or which were isolated using cDNA encoding a CRSP as a probe. The isolated DNA can have the respective regulatory sequences in the 5' and 3' flanks, e.g., promoters, enhancers, poly-A addition signals, and others.

IV. Making CRSPs

DNAs which encode a CRSP or fragments thereof can be obtained by chemical synthesis, screening cDNA libraries, or by screening genomic libraries prepared from a wide variety of cell lines or tissue samples.

These DNAs can be expressed in a wide variety of host cells for the synthesis of a full-length protein or fragments which can in turn, e.g., be used to generate polyclonal or monoclonal antibodies; for binding studies; for construction and expression of modified molecules; and for structure/function studies. Each CRSP or its fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, e.g., CRSP, or portions thereof, may be expressed as fusions with other proteins or possessing an epitope tag. Forms with a carboxy terminal FLAG® expression system epitope tag have been produced.

Expression vectors are typically self-replicating DNA or RNA constructs containing the desired antigen gene or its fragments, usually operably linked to appropriate genetic control elements that are recognized in a suitable host cell. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently from the host cell.

The vectors of this invention contain DNAs which encode a CRSP, or a fragment thereof, typically encoding, e.g., a biologically active polypeptide, or protein. The DNA can be under the control of a viral promoter and can encode a selection marker. This invention further contemplates use of such expression vectors which are capable of expressing eukaryotic cDNA coding for a CRSP in a prokaryotic or eukaryotic host, where the vector is compatible with the host and where the eukaryotic cDNA coding for the protein is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the protein or its fragments in various hosts using vectors that do not contain a replication origin that is recognized by the host cell. It is also possible to use vectors that cause integration of a CRSP gene or its fragments into the host DNA by recombination, or to integrate a promoter which controls expression of an endogenous gene.

Vectors, as used herein, contemplate plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector, but many other forms of vectors which serve an equivalent function are suitable for use herein. See, e.g., Pouwels, et al. (1985 and Supplements) *Cloning Vectors: A Laboratory Manual* Elsevier, N.Y.; and Rodriquez, et al. (eds.) (1988) *Vectors: A Survey of Molecular Cloning Vectors and Their Uses* Buttersworth, Boston, Mass.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and *Pichia*, and species of the genus Dictyostelium. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or its derivatives. Vectors that can be used to express CRSPs or CRSP fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses* 10:205-236 Buttersworth, Boston, Mass.

Lower eukaryotes, e.g., yeasts and Dictyostelium, may be transformed with CRSP sequence containing vectors. For purposes of this invention, the most common lower eukaryotic host is the baker's yeast, *Saccharomyces cerevisiae*. It will be used generically to represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are typically the preferred host cells for expression of the functionally active CRSP protein. In principle, many higher eukaryotic tissue culture cell lines may be used, e.g., insect baculovirus expression systems, whether from an invertebrate or vertebrate source. However, mammalian cells are preferred to achieve proper processing, both cotranslationally and posttranslationally. Transformation or transfection and propagation of such cells is routine. Useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (e.g., if genomic DNA is used), a polyadenylation site, and a transcription termination site. These vectors also may contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama, et al. (1985) *Mol. Cell Biol.* 5:1136-1142; pMC1neo Poly-A, see Thomas, et al. (1987) *Cell* 51:503-512; and a baculovirus vector such as pAC 373 or pAC 610.

It is likely that CRSPs need not be glycosylated to elicit biological responses. However, it will occasionally be desirable to express a CRSP polypeptide in a system which provides a specific or defined glycosylation pattern. In this case, the usual pattern will be that provided naturally by the expression system. However, the pattern will be modifiable by exposing the polypeptide, e.g., in unglycosylated form, to appropriate glycosylating proteins introduced into a heterologous expression system. For example, the CRSP gene may be co-transformed with one or more genes encoding mammalian or other glycosylating enzymes. It is further understood that over glycosylation may be detrimental to CRSP biological activity, and that one of skill may perform routine testing to optimize the degree of glycosylation which confers optimal biological activity.

A CRSP, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochem. Biophys. Acta* 988:427-454; Tse, et al. (1985) *Science* 230:1003-1008; and Brunner, et al. (1991) *J. Cell Biol.* 114:1275-1283.

Now that CRSPs have been characterized, fragments or derivatives thereof can be prepared by conventional processes for synthesizing peptides. These include processes such as are described in Stewart and Young (1984) *Solid Phase Peptide Synthesis* Pierce Chemical Co., Rockford, Ill.; Bodanszky and Bodanszky (1984) *The Practice of Peptide Synthesis* Springer-Verlag, New York, N.Y.; and Bodanszky (1984) *The Principles of Peptide Synthesis* Springer-Verlag, New York, N.Y. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The prepared protein and fragments thereof can be isolated and purified from the reaction mixture by means of peptide separation, for example, by extraction, precipitation, electrophoresis and various forms of chromatography, and the like. The CRSPs of this invention can be obtained in varying degrees of purity depending upon its desired use. Purification can be accomplished by use of known protein purification techniques or by the use of the antibodies or binding partners herein described, e.g., in immunoabsorbant affinity chromatography. This immunoabsorbant affinity chromatography is carried out by first linking the antibodies to a solid support and then contacting the linked antibodies with solubilized lysates of appropriate source cells, lysates of other cells expressing the ligand, or lysates or supernatants of cells producing the CRSPs as a result of recombinant DNA techniques, see below.

Multiple cell lines may be screened for one which expresses a CRSP at a high level compared with other cells. Various cell lines, e.g., a mouse thymic stromal cell line TA4, is screened and selected for its favorable handling properties.

Natural CRSPs can be isolated from natural sources, or by expression from a transformed cell using an appropriate expression vector. Purification of the expressed protein is achieved by standard procedures, or may be combined with engineered means for effective purification at high efficiency from cell lysates or supernatants. Epitope or other tags, e.g., FLAG® expression system tag sequences or His6 segments, can be used for such purification features.

V. Antibodies

Antibodies can be raised to various CRSPs, including individual, polymorphic, allelic, strain, or species variants, and fragments thereof, both in their naturally occurring (full-length) forms and in their recombinant forms. Additionally, antibodies can be raised to CRSPs in either their active forms or in their inactive forms. Anti-idiotypic antibodies may also be used.

A. Antibody Production

A number of immunogens may be used to produce antibodies specifically reactive with CRSP proteins. Recombinant protein is the preferred immunogen for the production of monoclonal or polyclonal antibodies. Naturally occurring protein may also be used either in pure or impure form. Synthetic peptides, made using the primate CRSP protein sequence described herein, may also used as an immunogen for the production of antibodies to CRSPs. Recombinant protein can be expressed in eukaryotic or prokaryotic cells as described herein, and purified as described. Naturally folded or denatured material can be used, as appropriate, for producing antibodies. Either monoclonal or polyclonal antibodies may be generated for subsequent use in immunoassays to measure the protein.

Methods of producing polyclonal antibodies are known to those of skill in the art. Typically, an immunogen, preferably a purified protein, is mixed with an adjuvant and animals are immunized with the mixture. The animal's immune response to the immunogen preparation is monitored by taking test bleeds and determining the titer of reactivity to the CRSP protein of interest. When appropriately high titers of antibody to the immunogen are obtained, usually after repeated immunizations, blood is collected from the animal and antisera are prepared. Further fractionation of the antisera to enrich for antibodies reactive to the protein can be done if desired. See, e.g., Harlow and Lane; or Coligan.

Monoclonal antibodies may be obtained by various techniques familiar to those skilled in the art. Typically, spleen cells from an animal immunized with a desired antigen are immortalized, commonly by fusion with a myeloma cell (see, Kohler and Milstein (1976) Eur. J. Immunol. 6:511-519, incorporated herein by reference). Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) Science 246:1275-1281.

Antibodies, including binding fragments and single chain versions, against predetermined fragments of CRSPs can be raised by immunization of animals with conjugates of the fragments with carrier proteins as described above. Monoclonal antibodies are prepared from cells secreting the desired antibody. These antibodies can be screened for binding to normal or defective CRSPs, or screened for agonistic or antagonistic activity, e.g., mediated through a receptor. These monoclonal antibodies will usually bind with at least a $K_D$ of about 1 mM, more usually at least about 300 µM, typically at least about 10 µM, more typically at least about 30 µM, preferably at least about 10 µM, and more preferably at least about 3 µM or better.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.) Lange Medical Publications, Los Altos, Calif., and references cited therein; Harlow and Lane (1988) *Antibodies: A Laboratory Manual* CSH Press; Goding (1986) Monoclonal Antibodies: Principles and Practice (2d ed.) Academic Press, New York, N.Y.; and particularly in Kohler and Milstein (1975) *Nature* 256:495-497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, e.g., Huse, et al. (1989) "Generation of a Large Combinatorial Library of the Immunoglobulin Repertoire in Phage Lambda," *Science* 246: 1275-1281; and Ward, et al. (1989) *Nature* 341:544-546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen, et al. (1989) *Proc. Nat'l Acad. Sci. USA* 86:10029-10033.

The antibodies of this invention are useful for affinity chromatography in isolating CRSP protein. Columns can be prepared where the antibodies are linked to a solid support, e.g., particles, such as agarose, SEPHADEX, or the like, where a cell lysate or supernatant may be passed through the column, the column washed, followed by increasing concentrations of a mild denaturant, whereby purified CRSP protein will be released.

The antibodies may also be used to screen expression libraries for particular expression products. Usually the antibodies used in such a procedure will be labeled with a moiety allowing easy detection of presence of antigen by antibody binding.

Antibodies to CRSPs may be used for the identification of cell populations expressing CRSPs. By assaying the expression products of cells expressing CRSPs it is possible to diagnose disease, e.g., immune-compromised conditions.

Antibodies raised against each CRSP will also be useful to raise anti-idiotypic antibodies. These will be useful in detecting or diagnosing various immunological conditions related to expression of the respective antigens.

B. Immunoassays

A particular protein can be measured by a variety of immunoassay methods. For a review of immunological and immunoassay procedures in general, see Stites and Terr (eds.) (1991) *Basic and Clinical Immunology* (7th ed.). Moreover, the immunoassays of the present invention can be performed in many configurations, which are reviewed extensively in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology,* Elsevier Science Publishers B.V., Amsterdam; and Harlow and Lane *Antibodies, A Laboratory Manual,* supra, each of which is incorporated herein by reference. See also Chan (ed.) (1987) *Immunoassay: A Practical Guide* Academic Press, Orlando, Fla.; Price and Newman (eds.) (1991) *Principles and Practice of Immunoassays* Stockton Press, NY; and Ngo (ed.) (1988) *Non-isotopic Immunoassays* Plenum Press, NY.

Immunoassays for measurement of CRSP proteins can be performed by a variety of methods known to those skilled in the art. In brief, immunoassays to measure the protein can be either competitive or noncompetitive binding assays. In competitive binding assays, the sample to be analyzed competes with a labeled analyte for specific binding sites on a capture agent bound to a solid surface. Preferably the capture agent is an antibody specifically reactive with CRSP proteins produced as described above. The concentration of labeled analyte bound to the capture agent is inversely proportional to the amount of free analyte present in the sample.

In a competitive binding immunoassay, the CRSP protein present in the sample competes with labeled protein for binding to a specific binding agent, for example, an antibody specifically reactive with the CRSP protein. The binding agent may be bound to a solid surface to effect separation of bound labeled protein from the unbound labeled protein. Alternately, the competitive binding assay may be conducted in liquid phase and a variety of techniques known in the art may be used to separate the bound labelled protein from the unbound labeled protein. Following separation, the amount of bound labeled protein is determined. The amount of protein present in the sample is inversely proportional to the amount of labeled protein binding.

Alternatively, a homogeneous immunoassay may be performed in which a separation step is not needed. In these immunoassays, the label on the protein is altered by the binding of the protein to its specific binding agent. This alteration in the labeled protein results in a decrease or increase in the signal emitted by label, so that measurement of the label at the end of the immunoassay allows for detection or quantitation of the protein.

Quantitation of CRSP proteins may also be performed using many of a variety of noncompetitive immunoassay methods. For example, a two-site, solid phase sandwich immunoassay may be used. In this type of assay, a binding agent for the protein, for example an antibody, is attached to a solid support. A second protein binding agent, which may also be an antibody, and which binds the protein at a different site, is labeled. After binding at both sites on the protein has occurred, the unbound labeled binding agent is removed and the amount of labeled binding agent bound to the solid phase is measured. The amount of labeled binding agent bound is directly proportional to the amount of protein in the sample.

Western blot analysis can be used to determine the presence of CRSP proteins in a sample. Electrophoresis is carried out, for example, on a tissue sample suspected of containing the protein. Following electrophoresis to separate the proteins, and transfer of the proteins to a suitable solid support, e.g., a nitrocellulose filter, the solid support is incubated with an antibody reactive with the protein. This antibody may be labeled, or alternatively may be detected by subsequent incubation with a second labeled antibody that binds the primary antibody.

The immunoassay formats described above employ labeled assay components. The label may be coupled directly or indirectly to the desired component of the assay according to methods well known in the art. A wide variety of labels and methods may be used. Traditionally, a radioactive label incorporating $^{3}H$, $^{125}I$, $^{35}S$, $^{14}C$, or $^{32}P$ was used. Non-radioactive labels include ligands which bind to labeled antibodies, fluorophores, chemiluminescent agents, enzymes, and antibodies which can serve as specific binding pair members for a labeled ligand. The choice of label depends on sensitivity required, ease of conjugation with the compound, stability requirements, and available instrumentation. For a review of various labelling or signal producing systems which may be used, see U.S. Pat. No. 4,391,904, which is incorporated herein by reference.

Antibodies reactive with a particular protein can also be measured by a variety of immunoassay methods. For a review of immunological and immunoassay procedures applicable to the measurement of antibodies by immunoassay techniques, see Stites and Terr (eds.) *Basic and Clinical Immunology* (7th ed.) supra; Maggio (ed.) *Enzyme Immunoassay,* supra; and Harlow and Lane *Antibodies, A Laboratory Manual,* supra.

In brief, immunoassays to measure antisera reactive with CRSP proteins can be either competitive or noncompetitive binding assays. In competitive binding assays, the sample analyte competes with a labeled analyte for specific binding sites on a capture agent bound to a solid surface. Preferably the capture agent is a purified recombinant CRSP protein produced as described above. Other sources of CRSP proteins, including isolated or partially purified naturally occurring protein, may also be used. Noncompetitive assays include sandwich assays, in which the sample analyte is bound between two analyte-specific binding reagents. One of the binding agents is used as a capture agent and is bound to a solid surface. The second binding agent is labeled and is used to measure or detect the resultant complex by visual or instrument means. A number of combinations of capture agent and labelled binding agent can be used. A variety of different immunoassay formats, separation techniques, and labels can be also be used similar to those described above for the measurement of CRSP proteins.

VI. Purified CRSPs

Specific embodiments of primate CRSP amino acid sequences are provided in SEQ ID NO: 2. The human sequence hybridizes to genes of mouse origin.

Purified protein or defined peptides are useful for generating antibodies by standard methods, as described above. Synthetic peptides or purified protein can be presented to an immune system to generate polyclonal and monoclonal antibodies. See, e.g., Coligan (1991) *Current Protocols in Immunology* Wiley/Greene, N.Y.; and Harlow and Lane (1989) *Antibodies: A Laboratory Manual* Cold Spring Harbor Press, NY, which are incorporated herein by reference. Alternatively, a CRSP receptor can be useful as a specific binding reagent, and advantage can be taken of its specificity of binding, for, e.g., purification of a CRSP ligand.

The specific binding composition can be used for screening an expression library made from a cell line which expresses a CRSP. Many methods for screening are available, e.g., standard staining of surface expressed ligand, or by panning. Screening of intracellular expression can also be performed by various staining or immunofluorescence procedures. The binding compositions could be used to affinity purify or sort out cells expressing the ligand.

The peptide segments, along with comparison to homologous genes, can also be used to produce appropriate oligonucleotides to screen a library. The genetic code can be used to select appropriate oligonucleotides useful as probes for screening. In combination with polymerase chain reaction (PCR) techniques, synthetic oligonucleotides will be useful in selecting desired clones from a library, including natural allelic an polymorphic variants.

The peptide sequences allow preparation of peptides to generate antibodies to recognize such segments, and allow preparation of oligonucleotides which encode such sequences. The sequence also allows for synthetic preparation, e.g., see Dawson, et al. (1994) *Science* 266:776-779. Since CRSPs appear to be secreted proteins, the gene will normally possess an N-terminal signal sequence, which is removed upon processing and secretion, and the putative cleavage site is between amino acids as indicated in Table 1, though it may be slightly in either direction.

VII. Physical Variants

This invention also encompasses proteins or peptides having substantial amino acid sequence similarity with an amino acid sequence of a CRSP. Natural variants include individual, polymorphic, allelic, strain, or species variants.

Amino acid sequence similarity, or sequence identity, is determined by optimizing residue matches, if necessary, by introducing gaps as required. This changes when considering conservative substitutions as matches. Physiocochemical conservative residue substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences include natural polymorphic, allelic, and interspecies variations in each respective protein sequence. Typical homologous proteins or peptides will have from 50-100% similarity (if gaps can be introduced), to 75-100% similarity (if conservative substitutions are included) with the amino acid sequence of the CRSP. Similarity measures will be at least about 50%, generally at least 60%, more generally at least 65%, usually at least 70%, more usually at least 75%, preferably at least 80%, and more preferably at least 80%, and in particularly preferred embodiments, at least 85% or more. See also Needleham, et al. (1970) *J. Mol. Biol.* 48:443-453; Sankoff, et al. (1983) *Time Warps, String Edits, and Macromolecules: The Theory and Practice of Sequence Comparison* Chapter One, Addison-Wesley, Reading, Mass.; and software packages from IntelliGenetics, Mountain View, Calif.; and the University of Wisconsin Genetics Computer Group, Madison, Wis.

Nucleic acids encoding primate CRSP proteins will often hybridize to the nucleic acid sequence of SEQ ID NO: 1 under stringent conditions. For example, nucleic acids encoding mouse CRSP proteins will normally hybridize to the nucleic acid of SEQ ID NO: 1 under stringent hybridization conditions. Generally, stringent conditions are selected to be about 10° C. lower than the thermal melting point (Tm) for the probe sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.2 molar at pH 7 and the temperature is at least about 50° C. Other factors may significantly affect the stringency of hybridization, including, among others, base composition and size of the complementary strands, the presence of organic solvents such as formamide, and the extent of base mismatching. A preferred embodiment will include nucleic acids which will bind to disclosed sequences in 50% formamide and 200 mM NaCl at 42° C.

An isolated CRSP nucleic acid sequence can be readily modified by nucleotide substitutions, nucleotide deletions, nucleotide insertions, and short inversions of nucleotide stretches. These modifications result in novel DNA sequences which encode CRSP antigens, their derivatives, or proteins having highly similar physiological, immunogenic, or antigenic activity.

Modified sequences can be used to produce mutant antigens or to enhance expression. Enhanced expression may involve gene amplification, increased transcription, increased translation, and other mechanisms. Such mutant CRSP derivatives include predetermined or site-specific mutations of the respective protein or its fragments. "Mutant CRSP" encompasses a polypeptide otherwise falling within the homology definition of the CRSP as set forth above, but having an amino acid sequence which differs from that of a CRSP as found in nature, whether by way of deletion, substitution, or insertion. In particular, "site specific mutant CRSP" generally includes proteins having significant similarity with a protein having a sequence of SEQ ID NO: 2, and as sharing various biological activities, e.g., antigenic or immunogenic, with those sequences, and in preferred embodiments contain most or all of the disclosed sequence. This applies also to polymorphic variants from different individuals. Similar concepts apply to different CRSP proteins, particularly those found in various warm blooded animals, e.g., mammals and birds. As stated before, it is emphasized that descriptions are generally meant to encompass other CRSP proteins, not limited to the mouse embodiments specifically discussed.

Although site specific mutation sites are predetermined, mutants need not be site specific. CRSP mutagenesis can be conducted by making amino acid insertions or deletions. Substitutions, deletions, insertions, or any combinations may be generated to arrive at a final construct. Insertions may include amino- or carboxyl-terminal fusions, e.g., epitope tags. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also, Sambrook, et al. (1989) and Ausubel, et al. (1987 and Supplements). The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with a CRSP polypeptide is a continuous protein molecule having sequences fused in a typical peptide linkage, typically made as a single translation product and exhibiting properties derived from each source peptide. One preferred embodiment is fusion of an Ig domain to the carboxy terminus of the protein. A similar concept applies to heterologous nucleic acid sequences.

In addition, new constructs may be made from combining similar functional domains from other proteins. Protein-binding or other segments may be "swapped" between different new fusion polypeptides or fragments, e.g., different CRSP embodiments. See, e.g., Cunningham, et al. (1989) *Science* 243:1330-1336; and O'Dowd, et al. (1988) *J. Biol. Chem.* 263:15985-15992. Thus, new chimeric polypeptides exhibiting new combinations of specificities will result from the functional linkage of protein-binding specificities and other functional domains.

VIII. Binding Agent:CRSP Protein Complexes

A CRSP protein that specifically binds to or that is specifically immunoreactive with an antibody generated against a defined immunogen, such as an immunogen consisting of the amino acid sequence of SEQ ID NO: 2, is typically determined in an immunoassay. The immunoassay uses a polyclonal antiserum which was raised to a protein of SEQ ID NO: 2. This antiserum is selected to have low crossreactivity against other chemokines and any such crossreactivity is removed by immunoabsorbtion prior to use in the immunoassay.

In order to produce antisera for use in an immunoassay, the protein of SEQ ID NO: 2, is isolated as described herein. For example, recombinant protein may be produced in a mammalian cell line. An inbred strain of mice or rats, such as balb/c mice, is immunized with a protein of SEQ ID NO: 2, using a standard adjuvant, such as Freund's adjuvant, and a standard immunization protocol (see Harlow and Lane, supra). Alternatively, a synthetic peptide, preferably near full length, derived from the sequences disclosed herein and conjugated to a carrier protein can be used an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against, e.g., known proteins exhibiting sequence similarity such as cytokines or growth factors, using a competitive binding immunoassay such as the one described in Harlow and Lane, supra, at pages 570-573. Preferably two family members are used in this determination in conjunction with various embodiments, e.g., mouse CRSPs.

Various forms of CRSPs are used to identify antibodies which are specifically bound. These proteins can be produced as recombinant proteins and isolated using standard molecular biology and protein chemistry techniques as described herein. Moreover, since the CRSPs seem to lack glycosylation sites, problems of post-translational modifications is lessened.

Immunoassays in the competitive binding format can be used for the crossreactivity determinations. For example, a protein of SEQ ID NO: 2 can be immobilized to a solid support. Proteins added to the assay compete with the binding of the antisera to the immobilized antigen. The ability of the above proteins to compete with the binding of the antisera to the immobilized protein is compared to the protein of SEQ ID NO: 2. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorbtion with the above-listed proteins.

The immunoabsorbed and pooled antisera are then used in a competitive binding immunoassay as described above to compare a second protein to the immunogen protein (e.g., the CRSP cysteine rich motifs of SEQ ID NO: 2). In order to make this comparison, the two proteins are each assayed at a wide range of concentrations and the amount of each protein required to inhibit 50% of the binding of the antisera to the immobilized protein is determined. If, e.g., the amount of the second protein required is less than twice the amount of the protein of SEQ ID NO: 2 that is required, then the second protein is said to specifically bind to an antibody generated to the immunogen.

It is understood that CRSP proteins are a family of homologous proteins that comprise multiple genes. For a particular gene product, such as the C23 CRSP protein, the term refers not only to the amino acid sequences disclosed herein, but also to other proteins that are polymorphic, allelic, non-allelic, or species variants. It is also understood that the term "primate CRSP" includes nonnatural mutations introduced by deliberate mutation using conventional recombinant technology such as single site mutation, or by excising very short sections of DNA encoding CRSP proteins, or by substituting new amino acids, or adding new amino acids. Such minor alterations must substantially maintain a particular feature, e.g., the immunoidentity of the original molecule and/or a biological activity. Thus, these alterations include proteins that are specifically immunoreactive with a designated naturally occurring CRSP protein, for example, the C23 CRSP protein shown in SEQ ID NO: 2. The biological properties of the altered proteins can be determined by expressing the protein in an appropriate cell line and measuring, e.g., a chemotactic effect. Particular protein modifications considered minor would include conservative substitution of amino acids with similar chemical properties, as described above for the CRSP family as a whole. By aligning, e.g., a protein optimally with the protein of SEQ ID NO: 2, and by using the conventional immunoassays described herein to determine immunoidentity, or by using chemotaxis assays, one can determine the protein compositions of the invention.

IX. Functional Variants

The blocking of physiological response to CRSPs may result from the inhibition of binding of the protein to its receptor, e.g., through competitive inhibition. Thus, in vitro assays of the present invention will often use isolated protein, membranes from cells expressing a recombinant membrane associated CRSP, soluble fragments comprising receptor binding segments of these proteins, or fragments attached to solid phase substrates. These assays will also allow for the diagnostic determination of the effects of either binding segment mutations and modifications, or protein mutations and modifications, e.g., protein analogs. This invention also contemplates the use of competitive drug screening assays, e.g., where neutralizing antibodies to antigen or receptor fragments compete with a test compound for binding to the protein. In this manner, the antibodies can be used to detect the presence of a polypeptide which shares one or more antigenic binding sites of the protein and can also be used to occupy binding sites on the protein that might otherwise interact with a receptor.

"Derivatives" of CRSP antigens include amino acid sequence mutants, glycosylation variants, and covalent or aggregate conjugates with other chemical moieties. Covalent derivatives can be prepared by linkage of functionalities to groups which are found in CRSP amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. While the primary sequences suggest the absence of glycosylation sites, the sequences may be modified to incorporate such. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine, or other moieties, including ribosyl groups or cross-linking reagents.

A major group of derivatives are covalent conjugates of the CRSP or fragments thereof with other proteins or polypeptides. These derivatives can be synthesized in recombinant culture such as N- or C-terminal fusions or by the use of agents known in the art for their usefulness in cross-linking proteins through reactive side groups. Preferred protein derivatization sites with cross-linking agents are at free amino groups, carbohydrate moieties, and cysteine residues.

Fusion polypeptides between CRSPs and other homologous or heterologous proteins are also provided. Many growth factors and cytokines are homodimeric entities, and a repeat construct may have various advantages, including lessened susceptibility to proteolytic degradation. Moreover, many receptors require dimerization to transduce a signal, and various dimeric proteins or domain repeats can be desirable. Heterologous polypeptides may be fusions between different surface markers, resulting in, e.g., a hybrid protein exhibiting receptor binding specificity. Likewise, heterologous fusions may be constructed which would exhibit a combination of properties or activities of the derivative proteins. Typical examples are fusions of a reporter polypeptide, e.g., luciferase, with a segment or domain of a protein, e.g., a receptor-binding segment, so that the presence or location of the fused protein may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812-816.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

This invention also contemplates the use of derivatives of CRSPs other than variations in amino acid sequence or glycosylation. Such derivatives may involve covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of ligands or other binding ligands. For example, a CRSP antigen can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-CRSP antibodies or its receptor. The CRSPs can also be labeled with a detectable group, e.g., radioiodinated by the chloramine T procedure, covalently bound to rare earth chelates, or conjugated to another fluorescent moiety for use in diagnostic assays. Purification of CRSPs may be effected by immobilized antibodies or receptor.

Isolated CRSP genes will allow transformation of cells lacking expression of corresponding CRSPs, e.g., either species types or cells which lack corresponding proteins and exhibit negative background activity. Expression of transformed genes will allow isolation of antigenically pure cell lines, with defined or single specie variants. This approach will allow for more sensitive detection and discrimination of the physiological effects of CRSP receptor proteins. Subcellular fragments, e.g., cytoplasts or membrane fragments, can be isolated and used.

X. Uses

The present invention provides reagents which will find use in diagnostic applications as described elsewhere herein, e.g., in the general description for developmental abnormalities, or below in the description of kits for diagnosis. Each of these embodiments of the family are associated rather specifically with an inflammatory or immunologially active tissue.

The cysteine rich nature makes the protein a good substrate for sulfhydryl reagents. It will be useful as a control for cysteine incorporation, and as a sample to test ability to sequence through those residues. The protein will also find use as a carbon source.

CRSP nucleotides, e.g., DNA or RNA, may be used as a component in a diagnostic assay. For instance, the nucleotide sequences provided may be labeled using, e.g., $^{32}$p or biotin and used to probe standard restriction fragment polymorphism blots, providing a measurable character to aid in distinguishing between individuals. Such probes may be used in well-known forensic techniques such as genetic fingerprinting. In addition, nucleotide probes made from CRSP sequences may be used in in situ assays to detect chromosomal abnormalities. For instance, rearrangements in the mouse chromosome encoding a CRSP gene may be detected via well-known in situ techniques, using CRSP probes in conjunction with other known chromosome markers.

Antibodies and other binding agents directed towards CRSP proteins or nucleic acids may be used to purify the corresponding CRSP molecule. As described in the Examples below, antibody purification of CRSP components is both possible and practicable. Antibodies and other binding agents may also be used in a diagnostic fashion to determine whether CRSP components are present in a tissue sample or cell population using well-known techniques described herein. Specific medical conditions correlating with expression of the respective embodiments is described. The ability to attach a binding agent to a CRSP provides a means to diagnose disorders associated with CRSP misregulation. Antibodies and other CRSP binding agents may also be useful as histological markers. As described in the examples below, CRSP expression is limited to specific tissue types. By directing a probe, such as an antibody or nucleic acid to a CRSP it is possible to use the probe to distinguish tissue and cell types in situ or in vitro.

This invention also provides reagents with significant therapeutic value. The CRSPs (naturally occurring or recombinant), fragments thereof, and antibodies thereto, along with compounds identified as having binding affinity to a CRSP, are useful in the treatment of conditions associated with abnormal physiology or development, including abnormal proliferation, e.g., inflammatory conditions, cancerous conditions, or degenerative conditions. Abnormal proliferation, regeneration, degeneration, and atrophy may be modulated by appropriate therapeutic treatment using the compositions provided herein. For example, a disease or disorder associated with abnormal expression or abnormal signaling by a CRSP is a target for an agonist or antagonist of the protein. The proteins likely play a role in regulation or development of various cells, e.g., lymphoid cells, which affect immunological responses.

Other abnormal developmental conditions are known in cell types shown to possess CRSP mRNA by northern blot analysis. See Berkow (ed.) *The Merck Manual of Diagnosis and Therapy,* Merck & Co., Rahway, N.J.; and Thorn, et al. *Harrison's Principles of Internal Medicine,* McGraw-Hill, N.Y. Developmental or functional abnormalities, e.g., of the immune system, cause significant medical abnormalities and conditions which may be susceptible to prevention or treatment using compositions provided herein. The role of epithelial cells in such conditions may be important.

Recombinant CRSP or CRSP antibodies can be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using antibodies or receptor or fragments thereof can identify compounds having binding affinity to CRSPs, including isolation of associated components. Subsequent biological assays can then be utilized to determine if the compound has intrinsic stimulating activity and is therefore a blocker or antagonist in that it blocks the activity of the protein. Likewise, a compound having intrinsic stimulating activity can activate the receptor and is thus an agonist in that it simulates the activity of a CRSP. This invention further contemplates the therapeutic use of antibodies to CRSPs as antagonists. This approach should be particularly useful with other CRSP species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index,* Merck & Co., Rahway, N.J. Dosage ranges would ordinarily be expected to be in amounts lower than 1 mM concentrations, typically less than about 10 µM concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

CRSPs, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa.; Avis, et al. (eds.) (1993) *Pharmaceutical Dosage Forms: Parenteral Medications* Dekker, N.Y.; Lieberman, et al. (eds.) (1990) *Pharmaceutical Dosage Forms: Tablets* Dekker, N.Y.; and Lieberman, et al. (eds.) (1990) *Pharmaceutical Dosage Forms: Disperse Systems* Dekker, N.Y. The therapy of this invention may be combined with or used in association with other therapeutic agents.

Both the naturally occurring and the recombinant forms of the CRSPs of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767-773, and other descriptions of chemical diversity libraries, which describe means for testing of binding affinity by a plurality of compounds. The development of suitable assays can be greatly facilitated by the availability of large amounts of purified, soluble CRSP as provided by this invention.

For example, antagonists can normally be found once the protein has been structurally defined. Testing of potential protein analogs is now possible upon the development of highly automated assay methods using a purified receptor. In particular, new agonists and antagonists will be discovered by using screening techniques described herein. Of particular importance are compounds found to have a combined binding affinity for multiple CRSP receptors, e.g., compounds which can serve as antagonists for species variants of a CRSP.

This invention is particularly useful for screening compounds by using recombinant protein in a variety of drug screening techniques. The advantages of using a recombinant protein in screening for specific ligands include: (a) improved renewable source of the CRSP from a specific source; (b) potentially greater number of ligands per cell giving better signal to noise ratio in assays; and (c) species variant specificity (theoretically giving greater biological and disease specificity).

One method of drug screening utilizes eukaryotic or prokaryotic host cells which are stably transformed with recombinant DNA molecules expressing a CRSP receptor. Cells may be isolated which express a receptor in isolation from any others. Such cells, either in viable or fixed form, can be used for standard ligand/receptor binding assays. See also, Parce, et al. (1989) *Science* 246:243-247; and Owicki, et al. (1990) *Proc. Nat'l Acad. Sci. USA* 87:4007-4011, which describe sensitive methods to detect cellular responses. Competitive assays are particularly useful, where the cells (source of CRSP) are contacted and incubated with a labeled receptor or antibody having known binding affinity to the ligand, such as $^{125}$I-antibody, and a test sample whose binding affinity to the binding composition is being measured. The bound and free labeled binding compositions are then separated to assess the degree of ligand binding. The amount of test compound bound is inversely proportional to the amount of labeled receptor binding to the known source. Any one of numerous techniques can be used to separate bound from free ligand to assess the degree of ligand binding. This separation step could typically involve a procedure such as adhesion to filters followed by washing, adhesion to plastic followed by washing, or centrifugation of the cell membranes. Viable cells could also be used to screen for the effects of drugs on CRSP mediated functions, e.g., second messenger levels, i.e., $Ca^{++}$; cell proliferation; inositol phosphate pool changes; and others. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus.

Another method utilizes membranes from transformed eukaryotic or prokaryotic host cells as the source of a CRSP. These cells are stably transformed with DNA vectors directing the expression of a CRSP, e.g., an engineered membrane bound form. Essentially, the membranes would be prepared from the cells and used in a receptor/ligand binding assay such as the competitive assay set forth above.

Still another approach is to use solubilized, unpurified or solubilized, purified CRSP from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to a CRSP antibody and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al., supra. Then all the pins are reacted with solubilized, unpurified or solubilized, purified CRSP antibody, and washed. The next step involves detecting bound CRSP antibody.

Rational drug design may also be based upon structural studies of the molecular shapes of the CRSP and other effectors or analogs. See, e.g., *Methods in Enzymology* vols 202 and 203. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography* Academic Press, NY A purified CRSP can be coated directly onto plates for use in the aforementioned drug screening techniques. However, non-neutralizing antibodies to these ligands can be used as capture antibodies to immobilize the respective ligand on the solid phase.

XI. Kits

This invention also contemplates use of CRSPs, fragments thereof, peptides, and their fusion products in a variety of diagnostic kits and methods for detecting the presence of CRSP or a CRSP receptor. Typically the kit will have a compartment containing either a defined CRSP peptide or gene segment or a reagent which recognizes one or the other, e.g., receptor fragments or antibodies.

A kit for determining the binding affinity of a test compound to a CRSP would typically comprise a test compound; a labeled compound, e.g., a receptor or antibody having known binding affinity for the CRSP; a source of CRSP (naturally occurring or recombinant); and a means for separating bound from free labeled compound, such as a solid phase for immobilizing the CRSP. Once compounds are screened, those having suitable binding affinity to the CRSP can be evaluated in suitable biological assays, as are well known in the art, to determine whether they act as agonists or antagonists to the receptor. The availability of recombinant CRSP polypeptides also provide well defined standards for calibrating such assays.

A preferred kit for determining the concentration of, for example, a CRSP in a sample would typically comprise a labeled compound, e.g., receptor or antibody, having known binding affinity for the CRSP, a source of CRSP (naturally occurring or recombinant), and a means for separating the bound from free labeled compound, for example, a solid phase for immobilizing the CRSP. Compartments containing reagents, and instructions, will normally be provided.

Antibodies, including antigen binding fragments, specific for the CRSP or ligand fragments are useful in diagnostic applications to detect the presence of elevated levels of CRSP and/or its fragments. Such diagnostic assays can employ lysates, live cells, fixed cells, immunofluorescence, cell cultures, body fluids, and further can involve the detection of antigens related to the ligand in a body fluid, e.g., serum, or the like. Diagnostic assays may be homogeneous (without a separation step between free reagent and antigen-CRSP complex) or heterogeneous (with a separation step). Various commercial assays exist, such as radioimmunoassay (RIA), enzyme-linked immunosorbentassay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to a CRSP or to a particular fragment thereof. Similar assays have also been extensively discussed in the literature. See, e.g., Harlow and Lane (1988) *Antibodies: A Laboratory Manual,* CSH Press, NY; Chan (ed.) (1987) *Immunoassay: A Practical Guide* Academic Press, Orlando, Fla.; Price and Newman (eds.) (1991) *Principles and Practice of Immunoassay* Stockton Press, NY; and Ngo (ed.) (1988) *Nonisotopic Immunoassay* Plenum Press, NY.

Anti-idiotypic antibodies may have similar use to diagnose presence of antibodies against a CRSP, as such may be diagnostic of various abnormal states. For example, overproduction of CRSP may result in production of various immunological or other medical reactions which may be diagnostic of abnormal physiological states, e.g., in cell growth, acitivation, or differentiation.

Frequently, the reagents for diagnostic assays are supplied in kits, so as to optimize the sensitivity of the assay. For the subject invention, depending upon the nature of the assay, the protocol, and the label, either labeled or unlabeled antibody or receptor, or labeled CRSP is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Many of the aforementioned constituents of the drug screening and the diagnostic assays may be used without modification, or may be modified in a variety of ways. For example, labeling may be achieved by covalently or non-covalently joining a moiety which directly or indirectly provides a detectable signal. In any of these assays, the protein, test compound, CRSP, or antibodies thereto can be labeled either directly or indirectly. Possibilities for direct labeling include label groups: radiolabels such as $^{125}I$, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free ligand, or alternatively the bound from the free test compound. The CRSP can be immobilized on various matrices followed by washing. Suitable matrices include plastic such as an ELISA plate, filters, and beads. Methods of immobilizing the CRSP to a matrix include, without limitation, direct adhesion to plastic, use of a capture antibody, chemical coupling, and biotin-avidin. The last step in this approach involves the precipitation of ligand/receptor or ligand/antibody complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457-1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a CRSP. These sequences can be used as probes for detecting levels of the CRSP message in samples from natural sources, or patients suspected of having an abnormal condition, e.g., cancer or developmental problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}P$. However, other techniques may also be employed, such as using biotin modified nucleotides for introduction into a polynucleotide. The biotin then serves as the site for binding to avidin or antibodies, which may be labeled with a wide variety of labels, such as radionuclides, fluorophores, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out using many conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89-97.

XII. Receptor Isolation

Having isolated a binding partner of a specific interaction, methods exist for isolating the counter-partner. See, Gearing, et al. (1989) *EMBO J.* 8:3667-3676. For example, means to label a CRSP without interfering with the binding to its receptor can be determined. For example, an affinity label or epitope tag can be fused to either the amino- or carboxyl-terminus of the ligand. An expression library can be screened for specific binding of the CRSP, e.g., by cell sorting, or other screening to detect subpopulations which express such a binding component. See, e.g., Ho, et al. (1993) *Proc. Nat'l Acad. Sci. USA* 90:11267-11271. Alternatively, a panning method may be used. See, e.g., Seed and Aruffo (1987) *Proc. Nat'l Acad. Sci. USA* 84:3365-3369. A two-hybrid selection system may also be applied making appropriate constructs with the available CRSP sequences. See, e.g., Fields and Song (1989) *Nature* 340:245-246.

Protein cross-linking techniques with label can be applied to isolate binding partners of a CRSP. This would allow identification of proteins which specifically interact with a CRSP, e.g., in a ligand-receptor like manner. It is likely that the receptor will be found by expression in a system which is capable of expressing a membrane protein in a form capable of exhibiting ligand binding capability.

The broad scope of this invention is best understood with reference to the following examples, which are not intended to limit the invention to specific embodiments.

EXAMPLES

I. General Methods

Many of the standard methods below are described or referenced, e.g., in Maniatis, et al. (1982) *Molecular Cloning, A Laboratory Manual* Cold Spring Harbor Laboratory, Cold Spring Harbor Press, NY; Sambrook, et al. (1989) *Molecular Cloning: A Laboratory Manual (*2d ed.) Vols. 1-3, CSH Press, NY; Ausubel, et al., *Biology* Greene Publishing Associates, Brooklyn, N.Y.; or Ausubel, et al. (1987 and Supplements) *Current Protocols in Molecular Biology* Wiley/Greene, NY; Innis, et al. (eds.) (1990) *PCR Protocols: A Guide to Methods and Applications* Academic Press, NY. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," *Methods in Enzmology* vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments (epitope tags), e.g., to a FLAG sequence or an equivalent which can be fused, e.g., via a protease-removable sequence. See, e.g., Hochuli (1989) *Chemische Industrie* 12:69-70; Hochuli (1990) "Purification of Recombinant Proteins with Metal Chelate Absorbent" in Setlow (ed.) *Genetic Engineering, Principle and Methods* 12:87-98, Plenum Press, NY; and Crowe, et al. (1992) *QIAexpress: The High Level Expression & Protein Purification System* QUIAGEN, Inc., Chatsworth, Calif.

Standard immunological techniques are described, e.g., in Coligan (1991) *Current Protocols in Immunology* Wiley/Greene, NY; and *Methods in Enzymology* volumes. 70, 73, 74, 84, 92, 93, 108, 116, 121, 132, 150, 162, and 163. Defensin assays are well knowne, and described, e.g., in Harwig, et al. (1994) *Methods in Enzymology* 236:160-172. Assays for neural cell biological activities are described, e.g., in Wouterlood (ed. 1995) *Neuroscience Protocols* modules 10, Elsevier; *Methods in Neurosciences* Academic Press; and *Neuromethods* Humana Press, Totowa, N.J. Methodology of developmental systems is described, e.g., in Meisami (ed.) *Handbook of Human Growth and Developmental Biology* CRC Press; and Chrispeels (ed.) *Molecular Techniques and Approaches in Developmental Biology* Interscience.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. cDNA Libraries

RNA is carefully extracted from the appropriate source to maintain full length integrity of the messenger. cDNA is made from appropariate cell types and fetal tissues, e.g., from 2 µg of high quality mRNA. Each library was typically quality controlled by three criteria: 1) Alkaline gel analysis of the first strand synthesis to evaluate size range of cDNA from >0.5-5 kb, indicating high quality RNA and a good predictor of large insert sizes in the final library. 2) Upon ligation of cDNA, the number of independent clones was greater than $1 \times 10^6$ clones before amplification. 3) Sequence analysis of randomly selected clones from each library typically revealed a high proportion of full length clones, and only very low levels of genomic or ribosomal RNA contamination (<5%). We found that, although standard RNA blot analysis of gene expression levels is somewhat more sensitive, a positive signal in a cDNA library is roughly comparable to RNA analysis, particularly in judging the presence or absence of a particular gene in a certain cell type or tissue. Large scale plasmid DNA preparation of amplified libraries was performed, e.g., using a Giga prep (Qiagen, Chatsworth, Calif.).

Southern Analysis: DNA (5 µg) from the primary amplified cDNA library was digested with appropriate restriction enzymes to release the inserts, run on a 1% agarose gel and transferred to a nylon membrane (Schleicher and Schuell, Keene, N.H.).

Samples for mRNA isolation include: peripheral blood mononuclear cells (monocytes, T cells, NK cells, granulocytes, B cells), resting (T 100); peripheral blood mononuclear cells, activated with anti-CD3 for 2, 6, 12 h pooled (T101); T cell, TH0 clone Mot 72, resting (T102); T cell, TH0 clone Mot 72, activated with anti-CD28 and anti-CD3 for 3, 6, 12 h pooled (T103); T cell, TH0 clone Mot 72, anergic treated with specific peptide for 2, 7, 12 h pooled (T104); T cell, TH1 clone HY06, resting (T107); T cell, TH1 clone HY06, activated with anti-CD28 and anti-CD3 for 3, 6, 12 h pooled (T108); T cell, TH1 clone HY06, anergic treated with specific peptide for 2, 6, 12 h pooled (T109); T cell, TH2 clone HY935, resting (T110); T cell, TH2 clone HY935, activated with anti-CD28 and anti-CD3 for 2, 7, 12 h pooled (T111); T cells CD4+CD45RO− T cells polarized 27 days in anti-CD28, IL-4, and anit IFN-g, TH2 polarized, activated with anti-CD3 and anti-CD28 4 h (T116); T cell tumor lines Jurkat and Hut78, resting (T117); T cell clones, pooled AD130.2, Tc783.12, Tc783.13, Tc783.58, Tc782.69, resting (Ti 118); T cell random gd T cell clones, resting (T119); Splenocytes, resting (B100); Splenocytes, activated with anti-CD40 and IL-4 (B101); B cell EBV lines pooled WT49, RSB, JY, CVIR, 721.221, RM3, HSY, resting (B102); B cell line JY, activated with PMA and ionomycin for 1, 6 h pooled (B103); NK 20 clones pooled, resting (K100); NK 20 clones pooled, activated with PMA and ionomycin for 6 h (K101); NKL clone, derived from peripheral blood of LGL leukemia patient, IL-2 treated (K106); NK cytotoxic clone 640-A30-1, resting (K107); hematopoietic precursor line TF1, activated with PMA and ionomycin for 1, 6 h pooled (C100); U937 premonocytic line, resting (M100); U937 premonocytic line, activated with PMA and ionomycin for 1, 6, h pooled (M101); elutriated monocytes, activated with LPS, IFNg, anti-IL-10 for 1, 2, 6, 12, 24 h pooled (M102); elutriated monocytes, activated with LPS, IFNg, IL-10 for 1, 2, 6, 12, 24 h pooled (M103); elutriated monocytes, activated with LPS, IFNg, anti-IL-10 for 4, 16 h pooled (M106); elutriated monocytes, activated with LPS, IFNg, IL-10 for 4, 16 h pooled (M107); elutriated monocytes, activated LPS for 1 h (M108); elutriated monocytes, activated LPS for 6 h (M109); DC 70% CD1a+, from CD34+ GM-CSF, TNFa 12 days, resting (D101); DC 70% CD1a+, from CD34+ GM-CSF, TNFa 12 days, activated with PMA and ionomycin for 1 hr (D102); DC 70% CD1a+, from CD34+ GM-CSF, TNFa 12 days, activated with PMA and ionomycin for 6 hr (D103); DC 95% CD1a+, from CD34+ GM-CSF, TNFa 12 days FACS sorted, activated with PMA and ionomycin for 1, 6 h pooled (D104); DC 95% CD14+, ex CD34+ GM-CSF, TNFa 12 days FACS sorted, activated with PMA and ionomycin 1, 6 hr pooled (D105); DC CD1a+ CD86+, from CD34+ GM-CSF, TNFa 12 days FACS sorted, activated with PMA and ionomycin for 1, 6 h pooled (D106); DC from monocytes GM-CSF, IL-4 5 days, resting (D107); DC from monocytes GM-CSF, IL-4 5 days, resting (D108); DC from monocytes GM-CSF, IL-4 5 days, activated LPS 4, 16 h pooled (D109); DC from monocytes GM-CSF, IL-4 5 days, activated TNFa, monocyte supe for 4, 16 h pooled (D110); leiomyoma L11 benign tumor (X101); normal myometrium M5 (O115); malignant leiomyosarcoma GS1 (X103); lung fibroblast sarcoma line MRC5, activated with PMA and ionomycin for 1, 6 h pooled (C101); kidney epithelial carcinoma cell line CHA, activated with PMA and ionomycin for 1, 6 h pooled (C102); kidney fetal 28 wk male (O100); lung fetal 28 wk male (O101); liver fetal 28 wk male (O102); heart fetal 28 wk male (O103); brain fetal 28 wk male (O104); gallbladder fetal 28 wk male (O106); small intestine fetal 28 wk male (O107); adipose tissue fetal 28 wk male (O108); ovary fetal 25 wk female (O109); uterus fetal 25 wk female (O110); testes fetal 28 wk male (O111); spleen fetal 28 wk male (O112); adult placenta 28 wk (O113); and tonsil inflamed, from 12 year old (X100).

III. Isolation of C23 CRSP Embodiment

A clone encoding the human C23 CRSP is isolated from a natural source by many different possible methods. Given the sequences provided herein, PCR primers or hybridization probes are selected and/or constructed to isolate either genomic DNA segments or cDNA reverse transcripts. Appropriate cell sources include inflamed tonsil tissue. Genetic and polymorphic or allelic variants are isolated by screening a population of individuals, e.g., other primates, etc.

PCR based detection is performed by standard methods, preferably using primers from opposite ends of the coding sequence, but flanking segments might be selected for specific purposes.

Alternatively, hybridization probes are selected. Particular AT or GC contents of probes are selected depending upon the expected homology and mismatching expected. Appropriate stringency conditions are selected to balance an appropriate positive signal to background ratio. Successive washing steps are used to collect clones of greater homology.

Further clones are isolated using an antibody based selection procedure. Standard expression cloning methods are applied including, e.g., FACS staining of membrane associated expression product. The antibodies are used to identify clones producing a recognized protein. Alternatively, antibodies are used to purify a specific CRSP, with protein sequencing and standard means to isolate a gene encoding that protein.

Genomic sequence based methods will also allow for identification of sequences naturally available, or otherwise, which exhibit homology to the provided sequences.

IV. Isolation of Other Primate CRSP Clones

Similar methods are used as above to isolate an appropriate primate CRSP gene. Similar source materials as indicated above are used to isolate natural genes, including genetic, polymorphic, allelic, or strain variants. Species variants are also isolated using similar methods.

Antigenic methods may be used to immunoprecipitate related molecules. In particular, native proteins likely share tertiary structure, as the cysteines are both numerous and conserved, and will likely cross react.

Additional data suggests that the rodent genes encoding the various embodiments may be genetically linked. Isolation of the genomic region encoding one embodiment is likely to lead, using appropriate methods of chromosome walking or other methods, to the genes of other embodiments. PCR methodology may make use of the highly conserved segments of sequence, as indicated above. Particularly useful PCR primers spanning those conserved regions include, for the coding strand, TGT GGC THY GSC TGT GGM TCK TGG, and for the non-coding strand, CA GCA GCG SGC WSH KGT CCA GTC (SEQ ID NO: 3 and 4). These highly conserved primer segments are likely to be also useful to isolate species counterparts.

The human gene cross-hybridizes with certain mouse isolates. See Franz-Bacon, et al., which is filed in the same date as this.another application (Attorney Docket Number DX0743) filed by the same inventors, which is incorporated herein by reference.

V. Expression; Purification; Characterization

With an appropriate clone from above, the coding sequence is inserted into an appropriate expression vector. This may be in a vector specifically selected for a prokaryote, yeast, insect, or higher vertebrate, e.g., mammalian expression system. Standard methods are applied to produce the gene product, preferably as a soluble secreted molecule, but will, in certain instances, also be made as an intracellular protein. Intracellular proteins typically require cell lysis to recover the protein, and insoluble inclusion bodies are a common starting material for further purification. Particularly preferred methods are to express in a eukaryotic, e.g., mouse cell. The protein has been well expressed and secreted.

With a clone encoding a primate CRSP, recombinant production means are used, although natural forms may be purified from appropriate sources. The protein product is purified by standard methods of protein purification, in certain cases, e.g., coupled with immunoaffinity methods. Immunoaffinity methods are used either as a purification step, as described above, or as a detection assay to determine the separation properties of the protein.

Preferably, the protein is secreted into the medium, and the soluble product is purified from the medium in a soluble form. Alternatively, as described above, inclusion bodies from prokaryotic expression systems are a useful source of material. Typically, the insoluble protein is solubilized from the inclusion bodies and refolded using standard methods. Purification methods are developed as described above.

The product of the purification method described above is characterized to determine many structural features. Standard physical methods are applied, e.g., amino acid analysis and protein sequencing. The resulting protein is subjected to CD spectroscopy and other spectroscopic methods, e.g., NMR, ESR, mass spectroscopy, etc. The product is characterized to determine its molecular form and size, e.g., using gel chromatography and similar techniques. Understanding of the chromatographic properties will lead to more gentle or efficient purification methods. Preliminary analysis suggests that the human C23 is a covalently linked dimer (or possibly polymer) of subunits. Two of the mouse embodiments are also likely covalently linked dimers. The monomer forms exhibit reducing gel PAGE mobility corresponding to about 7.5-8 kDa.

Prediction of glycosylation sites may be made, e.g., as reported in Hansen, et al. (1995) *Biochem. J.* 308:801-813. However, these seem not to possess obvious sites.

VI. Preparation of Antibodies Against CRSP

With protein produced, as above, appropriate animals are immunized to produce antibodies. Polyclonal antiserum is raised using non-purified antigen, though the resulting serum will exhibit higher background levels. Preferably, the antigen is purified using standard protein purification techniques, including, e.g., affinity chromatography using polyclonal serum indicated above. Presence of specific antibodies is detected using defined synthetic peptide fragments.

Polyclonal serum is raised against a purified antigen, purified as indicated above, or using synthetic peptides. A series of overlapping synthetic peptides which encompass all of the full length sequence, if presented to an animal, will produce serum recognizing most linear epitopes on the protein. Such an antiserum is used to affinity purify protein, which is, in turn, used to introduce intact full length protein into another animal to produce-another antiserum preparation.

Similar techniques are used to generate induce monoclonal antibodies to either unpurified antigen, or, preferably, purified antigen. Antibody fragments may also be prepared from these antibodies.

VII. Cellular and Tissue Distribution

Distribution of the protein or gene products are determined, e.g., using immunohistochemistry with an antibody reagent, as produced above, or by screening for nucleic acids encoding the CRSP. Either hybridization or PCR methods are used to detect DNA, cDNA, or message content. Histochemistry allows determination of the specific cell types within a tissue which express higher or lower levels of message or DNA. Antibody techniques are useful to quantitate protein in a biological sample, including a liquid or tissue sample. Immunoassays are developed to quantitate protein.

Hybridization techniques were applied. For example, adult Swiss Webster mice (Simonsen Labs, Gilroy, Calif.) were euthanized in a $CO_2$ atmosphere and tissues were dissected. Pregnant Swiss Webster mice were euthanized at 15 days post-coitus and embryonic tissues were dissected. Tissues were either snap frozen for RNA isolation or frozen in OCT medium (Miles, Elkhart, Ind.) for cryostat sectioning. Total cellular RNA was isolated from tissues by the RNAzol method (Teltest, Friendswood, Tex.). The RNA can be used to generate cDNA libraries, thus immortalizing RNA profiles of rare or very small cell populations.

"Reverse northerns" are blots from cDNA libraries with the inserts removed, and the size determinations are based upon the size of inserts in the cDNA library, and reflect the lengths found in the cDNA library inserts, which may be less than full length where the reverse transcription was not full length. As such, size determinations there are not reflective of the natural sizes.

The C23 embodiment was originally isolated from a natural human source. It is highly expressed in the inflamed tonsil sample, and is expressed in elutriated monocytes, activated with LPS, IFNg, anti-IL-10 for 1, 2, 6, 12, 24 h pooled (M102); elutriated monocytes, activated with LPS, IFNg, IL-10 for 1, 2, 6, 12, 24 h pooled (M103); peripheral blood mononuclear cells (monocytes, T cells, NK cells, granulocytes, B cells), resting (T100); U937 premonocytic line, resting (M100); elutriated monocytes, activated with LPS, IFNg, IL-10 for 4, 16 h pooled (M107). A detectable signal is found in DC from monocytes GM-CSF, IL-4 5 days, resting (D108); DC from monocytes GM-CSF, IL-4 5 days, activated LPS 4, 16 h pooled (D109); DC from monocytes GM-CSF, IL-4 5 days, activated TNFa, monocyte supe for 4, 16 h pooled (D110). It was not detected in any of the other listed samples tested.

This distribution suggests that the C23 is important in an inflammatory response, and is found in immunologically relevant cell types.

Because of the highly specific distribution, similar tissue samples in other species will be the preferred targets for identifying other species counterparts, e.g., to primate.

VIII. Chromosomal Mapping

The CRSP genes can be mapped to the human chromosome. Observations suggest that mouse CRSPs are linked. A BIOS Laboratories (New Haven, Conn.) mouse somatic cell hybrid panel can be combined with PCR.

Chromosomal mapping may be useful to isolate other family members where the genes are genetically linked. For example, using the C23 clone, chromosome walking analysis coupled with the significant homology in nucleotide sequence, will allow identification of additional new family members.

IX. Isolation of a Receptor

A labeled CRSP can be used as a specific binding reagent to identify its binding partner, by taking advantage of its specificity of binding, much like an antibody would be used. A binding reagent is either labeled as described above, e.g., fluorescence or otherwise, or immobilized to a substrate for panning methods. The typical chemokine receptor is a seven transmembrane receptor; and cytokine or growth hormone receptors are integral membrane proteins.

The binding composition, e.g., CRSP, is used to screen an expression library made from a cell line which expresses a binding partner, i.e. receptor. Standard staining techniques are used to detect or sort intracellular or surface expressed receptor, or surface expressing transformed cells are screened by panning. Screening of intracellular expression is performed by various staining or immunofluorescence procedures. See also McMahan, et al. (1991) *EMBO J.* 10:2821-2832.

For example, on day 0, precoat 2-chamber permanox slides with 1 ml per chamber of fibronectin, 10 ng/ml in PBS, for 30 min at room temperature. Rinse once with PBS. Then plate COS cells at $2-3\times10^5$ cells per chamber in 1.5 ml of growth media. Incubate overnight at 37° C.

On day 1 for each sample, prepare 0.5 ml of a solution of 66 µg/ml DEAE-dextran, 66 µM chloroquine, and 4 µg DNA in serum free DME. For each set, a positive control is prepared, e.g., of a growth factor, cytokine, or chemokine cDNA at 1 and ½00 dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at −80° C. after all liquid is removed. For each chamber, 0.5 ml incubations are performed as follows. Add HBSS/saponin (0.1%) with 32 µl/ml of 1 M $NaN_3$ for 20 min. Cells are then washed with HBSS/saponin 1×. Add CRSP or CRSP/antibody complex to cells and incubate for 30 min. Wash cells twice with HBSS/saponin. If appropriate, add first antibody for 30 min. Add second antibody, e.g., Vector anti-mouse antibody, at ½00 dilution, and incubate for 30 min. Prepare ELISA solution, e.g., Vector Elite ABC horseradish peroxidase solution, and preincubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of $H_2O_2$ per 5 ml of glass distilled water. Carefully remove chamber and rinse slide in water. Air dry for a few minutes, then add 1 drop of Crystal Mount and a cover slip. Bake for 5 min at 85-90° C.

Evaluate positive staining of pools and pregressively subclone to isolation of single genes responsible for the binding.

Alternatively, CRSP reagents are used to affinity purify or sort out cells expressing a receptor. See, e.g., Sambrook, et al. or Ausubel, et al.

Another strategy is to screen for a membrane bound receptor by panning. The receptor cDNA is constructed as described above. The ligand can be immobilized and used to immobilize expressing cells. Immobilization may be achieved by use of appropriate antibodies which recognize, e.g., a FLAG® expression system tag sequence of a chemokine fusion construct, or by use of antibodies raised against the first antibodies. Recursive cycles of selection and amplification lead to enrichment of appropriate clones and eventual isolation of receptor expressing clones.

Phage expression libraries can be screened by chemokine. Appropriate label techniques, e.g., anti-FLAG antibodies, will allow specific labeling of appropriate clones.

All references cited herein are incorporated herein by reference to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. An isolated polypeptide comprising the sequence of residues 1 to 90 of SEQ ID NO: 2.

2. The isolated polypeptide of claim 1 comprising the sequence of residues −18 to 90 of SEQ ID NO: 2.

3. A composition comprising the isolated polypeptide of claim 1 and a carrier, wherein said carrier comprises water, saline, or buffer.

4. A composition comprising the isolated polypeptide of claim 1 and a carrier, wherein said carrier is formulated for oral, rectal, nasal, topical, or parenteral administration.

5. The isolated polypeptide of claim 1 further comprising a detection or purification tag.

6. A kit comprising:
   a) the isolated polypeptide of claim 1; and
   b) instructions for use of the polypeptide.

7. An isolated polypeptide comprising the sequence of residues 33 to 86 of SEQ ID NO: 2.

* * * * *

UNITED STATES PATENT AND TRADEMARK OFFICE
CERTIFICATE OF CORRECTION

| | | |
|---|---|---|
| PATENT NO. | : 7,482,426 B2 | Page 1 of 1 |
| APPLICATION NO. | : 10/246983 | |
| DATED | : January 27, 2009 | |
| INVENTOR(S) | : Franz-Bacon et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 548 days Delete the phrase "by 548 days" and insert -- by 668 days --

Signed and Sealed this

Twenty-second Day of December, 2009

David J. Kappos
*Director of the United States Patent and Trademark Office*